United States Patent
Solomon et al.

(10) Patent No.: US 10,646,292 B2
(45) Date of Patent: May 12, 2020

(54) ELECTRO-MECHANICAL STRAP STACK IN ROBOTIC ARMS

(75) Inventors: Todd R. Solomon, San Jose, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 2553 days.

(21) Appl. No.: 11/611,850

(22) Filed: Dec. 15, 2006

(65) Prior Publication Data

US 2008/0021440 A1 Jan. 24, 2008

Related U.S. Application Data

(63) Continuation-in-part of application No. 10/957,077, filed on Sep. 30, 2004, now Pat. No. 7,594,912.

(Continued)

(51) Int. Cl.
 *A61B 34/37* (2016.01)
 *B25J 9/10* (2006.01)
 (Continued)

(52) U.S. Cl.
 CPC .............. *A61B 34/37* (2016.02); *A61B 34/30* (2016.02); *A61B 34/71* (2016.02); *B25J 9/1045* (2013.01);
 (Continued)

(58) Field of Classification Search
 CPC ..... A61B 19/2203; A61B 34/30; A61B 34/37; A61B 34/71; A61B 90/361;
 (Continued)

(56) References Cited

U.S. PATENT DOCUMENTS

| 369,023 A | 8/1887 | Newell |
| 586,731 A | 7/1897 | Monroe |

(Continued)

FOREIGN PATENT DOCUMENTS

| CH | 48243 A | 12/1969 |
| CH | 482439 | 12/1969 |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J., title page and table of contents only.

(Continued)

*Primary Examiner* — John R Downey

(57) ABSTRACT

In one embodiment of the invention, a strap drive-train for use in a robotic arm to enable movement of a linkage assembly of the robotic arm is provided. The linkage assembly includes a plurality of links pivotally coupled in series together at a plurality of joints, respectively, for movement of the robotic arm about a pitch axis. The strap drive-train includes a first driver pulley rigidly coupled to a link of the plurality of links and a second driver pulley rigidly coupled to another link of the plurality of links. The electro-mechanical strap stack includes at least one of a ground strap and an electrical cable strap in a stacked configuration with a drive strap, wherein the electro-mechanical strap stack is connected between the first driver pulley and the second driver pulley through a middle link.

30 Claims, 14 Drawing Sheets

Related U.S. Application Data

(60) Provisional application No. 60/752,788, filed on Dec. 21, 2005, provisional application No. 60/752,514, filed on Dec. 20, 2005.

(51) Int. Cl.
*A61B 34/00* (2016.01)
*A61B 34/30* (2016.01)
*A61B 17/00* (2006.01)
*A61B 90/00* (2016.01)

(52) U.S. Cl.
CPC ... *A61B 90/361* (2016.02); *A61B 2017/00477* (2013.01); *A61B 2034/305* (2016.02); *A61B 2034/715* (2016.02)

(58) Field of Classification Search
CPC .... A61B 2034/715; A61B 2017/00477; A61B 34/70; B25J 9/1045
USPC .......................... 600/100–152, 1; 606/1, 130
See application file for complete search history.

(56) References Cited

U.S. PATENT DOCUMENTS

| | | | |
|---|---|---|---|
| 669,393 A | 3/1901 | Henry | |
| 1,515,335 A | 11/1924 | Bosco | |
| 1,597,152 A | 8/1926 | Heintz | |
| 1,700,468 A | 1/1929 | Clutter et al. | |
| 2,027,275 A | 1/1936 | Foster | |
| D134,917 S | 1/1943 | Eubanks | |
| 2,331,382 A | 10/1943 | Eubanks | |
| 2,815,697 A | 12/1957 | Saunders-Singer | |
| 3,011,034 A | 11/1961 | Laviana et al. | |
| 3,025,647 A | 3/1962 | Moody | |
| 3,193,633 A | 7/1965 | Netzel et al. | |
| 3,463,329 A | 8/1969 | Gartner | |
| 3,500,692 A | 3/1970 | Arlon et al. | |
| 3,695,215 A | 10/1972 | Theodore | |
| 3,736,056 A * | 5/1973 | Burnet et al. | 399/216 |
| 3,739,649 A | 6/1973 | Pacini et al. | |
| 3,813,843 A | 6/1974 | Wooldridge et al. | |
| 3,872,960 A | 3/1975 | Gabor | |
| 3,954,282 A | 5/1976 | Hege | |
| 3,967,240 A * | 6/1976 | Young | B60Q 1/38 340/332 |
| 3,976,206 A * | 8/1976 | Flatau | B25J 3/00 74/96 |
| 4,030,376 A * | 6/1977 | Baudoin | B25J 3/00 474/111 |
| 4,143,445 A | 3/1979 | Fougman | |
| 4,260,319 A | 4/1981 | Motoda et al. | |
| 4,312,432 A | 1/1982 | Sugawa | |
| 4,362,525 A | 12/1982 | Sproul | |
| 4,396,919 A | 8/1983 | Speicher | |
| 4,486,183 A | 12/1984 | Posiviata et al. | |
| 4,537,084 A | 8/1985 | Passemard et al. | |
| 4,543,033 A | 9/1985 | Czermak et al. | |
| 4,696,501 A | 9/1987 | Webb | |
| 4,697,467 A | 10/1987 | Ando | |
| 4,728,252 A | 3/1988 | Lada et al. | |
| 4,897,015 A | 1/1990 | Abbe et al. | |
| 4,903,536 A | 2/1990 | Salisbury, Jr. | |
| 4,921,393 A | 5/1990 | Andeen et al. | |
| 4,923,053 A * | 5/1990 | Daniels | F16L 3/01 901/16 |
| 5,060,532 A | 10/1991 | Barker | |
| 5,074,539 A | 12/1991 | Wells et al. | |
| 5,078,140 A | 1/1992 | Kwoh | |
| 5,103,263 A * | 4/1992 | Moore et al. | 399/163 |
| 5,129,911 A | 7/1992 | Siczek et al. | |
| 5,149,057 A | 9/1992 | Meurer | |
| 5,150,937 A | 9/1992 | Yakou | |
| 5,157,980 A | 10/1992 | Chezzi | |
| 5,184,601 A | 2/1993 | Putman | |
| 5,203,247 A | 4/1993 | D'Arcy | |
| 5,209,747 A | 5/1993 | Knoepfler | |
| 5,217,003 A | 6/1993 | Wilk | |
| 5,217,453 A | 6/1993 | Wilk | |
| 5,219,351 A | 6/1993 | Teubner et al. | |
| 5,222,409 A | 6/1993 | Dalakian | |
| 5,257,998 A | 11/1993 | Ota et al. | |
| 5,273,039 A | 12/1993 | Fujiwara et al. | |
| 5,279,309 A | 1/1994 | Taylor et al. | |
| 5,329,800 A | 7/1994 | Herdzina et al. | |
| 5,333,986 A | 8/1994 | Mizukami et al. | |
| 5,339,799 A | 8/1994 | Kami et al. | |
| 5,339,929 A | 8/1994 | Chern | |
| 5,343,385 A | 8/1994 | Joskowicz et al. | |
| 5,353,202 A * | 10/1994 | Ansell et al. | 361/818 |
| 5,368,015 A | 11/1994 | Wilk | |
| 5,397,323 A | 3/1995 | Taylor et al. | |
| 5,402,801 A | 4/1995 | Taylor | |
| 5,417,210 A | 5/1995 | Funda et al. | |
| 5,427,581 A | 6/1995 | McGrath et al. | |
| 5,445,166 A | 8/1995 | Taylor | |
| 5,458,479 A | 10/1995 | Minghetti | |
| 5,479,929 A | 1/1996 | Cooper et al. | |
| 5,572,999 A | 11/1996 | Funda et al. | |
| 5,599,268 A | 2/1997 | Andersson et al. | |
| 5,630,431 A | 5/1997 | Taylor | |
| 5,682,795 A | 11/1997 | Solomon et al. | |
| 5,695,500 A | 12/1997 | Taylor et al. | |
| 5,697,939 A | 12/1997 | Kubota et al. | |
| 5,710,870 A * | 1/1998 | Ohm | B25J 3/04 700/245 |
| 5,749,362 A | 5/1998 | Funda et al. | |
| 5,762,458 A | 6/1998 | Wang et al. | |
| 5,778,730 A * | 7/1998 | Solomon et al. | 901/21 |
| 5,792,135 A * | 8/1998 | Madhani et al. | 606/1 |
| 5,794,487 A | 8/1998 | Solomon et al. | |
| 5,800,423 A | 9/1998 | Jensen | |
| 5,808,665 A | 9/1998 | Green | |
| 5,813,282 A | 9/1998 | Azuma | |
| 5,815,640 A | 9/1998 | Wang et al. | |
| 5,817,084 A | 10/1998 | Jensen | |
| 5,841,950 A | 11/1998 | Wang et al. | |
| 5,855,583 A | 1/1999 | Wang et al. | |
| 5,876,325 A | 3/1999 | Mizuno et al. | |
| 5,878,193 A | 3/1999 | Wang et al. | |
| 5,879,001 A | 3/1999 | Perego | |
| 5,907,664 A | 5/1999 | Wang et al. | |
| 5,931,832 A | 8/1999 | Jensen | |
| 5,967,112 A | 10/1999 | Haga et al. | |
| 6,001,108 A | 12/1999 | Wang et al. | |
| 6,007,550 A | 12/1999 | Wang et al. | |
| 6,106,511 A | 8/2000 | Jensen | |
| 6,116,197 A | 9/2000 | Tsunoda et al. | |
| 6,132,368 A | 10/2000 | Cooper | |
| 6,167,686 B1 | 1/2001 | Becker et al. | |
| 6,206,903 B1 | 3/2001 | Ramans | |
| 6,220,106 B1 | 4/2001 | Hayashi | |
| 6,246,200 B1 * | 6/2001 | Blumenkranz | A61B 34/70 901/15 |
| 6,309,403 B1 * | 10/2001 | Minor et al. | 606/205 |
| 6,324,934 B1 | 12/2001 | Monaghan | |
| 6,346,072 B1 | 2/2002 | Cooper | |
| 6,367,608 B1 | 4/2002 | Franceschi | |
| 6,371,952 B1 | 4/2002 | Madhani et al. | |
| 6,394,998 B1 | 5/2002 | Wallace et al. | |
| 6,406,472 B1 | 6/2002 | Jensen | |
| 6,428,266 B1 | 8/2002 | Solomon et al. | |
| 6,432,112 B2 | 8/2002 | Brock et al. | |
| 6,441,577 B2 | 8/2002 | Blumenkranz et al. | |
| 6,451,027 B1 | 9/2002 | Cooper et al. | |
| 6,594,552 B1 | 7/2003 | Nowlin et al. | |
| 6,659,939 B2 | 12/2003 | Moll et al. | |
| 6,676,669 B2 | 1/2004 | Charles et al. | |
| 6,699,235 B2 | 3/2004 | Wallace et al. | |
| 6,702,805 B1 * | 3/2004 | Stuart | 606/1 |
| 6,737,826 B2 | 5/2004 | Gilchrist | |
| 6,758,843 B2 | 7/2004 | Jensen | |
| 6,786,896 B1 | 9/2004 | Madhani et al. | |
| 6,788,018 B1 | 9/2004 | Blumenkranz | |

(56) References Cited

U.S. PATENT DOCUMENTS

| | | | |
|---|---|---|---|
| 6,871,643 B2 | 3/2005 | Cooper et al. | |
| 6,923,612 B2* | 8/2005 | Hansl | B65G 1/0435 |
| | | | 414/277 |
| 6,969,385 B2 | 11/2005 | Moreyra | |
| 7,021,173 B2 | 4/2006 | Stoianovici et al. | |
| 7,101,363 B2* | 9/2006 | Nishizawa et al. | 606/1 |
| 7,108,688 B2 | 9/2006 | Jensen | |
| 7,124,657 B2 | 10/2006 | Nagai et al. | |
| 7,316,681 B2 | 1/2008 | Madhani et al. | |
| 7,395,606 B2* | 7/2008 | Crampton | 33/503 |
| 7,422,592 B2 | 9/2008 | Morley et al. | |
| 7,594,912 B2 | 9/2009 | Cooper et al. | |
| 7,644,906 B2 | 1/2010 | Rodrigue et al. | |
| 7,854,738 B2 | 12/2010 | Lee et al. | |
| 7,865,266 B2 | 1/2011 | Moll et al. | |
| 7,935,130 B2 | 5/2011 | Williams et al. | |
| 7,947,050 B2 | 5/2011 | Lee et al. | |
| 7,947,051 B2 | 5/2011 | Lee et al. | |
| 8,062,288 B2 | 11/2011 | Cooper et al. | |
| 8,256,319 B2 | 9/2012 | Cooper et al. | |
| 8,281,683 B2 | 10/2012 | Garrec et al. | |
| 8,347,755 B2 | 1/2013 | Bennett et al. | |
| 8,347,756 B2 | 1/2013 | Bennett et al. | |
| 8,365,633 B2 | 2/2013 | Simaan et al. | |
| 8,512,316 B2 | 8/2013 | Jinno et al. | |
| 8,562,594 B2 | 10/2013 | Cooper et al. | |
| 2001/0027313 A1 | 10/2001 | Shimmura et al. | |
| 2002/0082612 A1 | 6/2002 | Moll et al. | |
| 2002/0091374 A1 | 7/2002 | Cooper | |
| 2003/0221504 A1 | 12/2003 | Stoianovici et al. | |
| 2003/0233102 A1 | 12/2003 | Nakamura et al. | |
| 2005/0043718 A1 | 2/2005 | Madhani et al. | |
| 2005/0241236 A1 | 11/2005 | Smith | |
| 2006/0074406 A1* | 4/2006 | Cooper et al. | 606/1 |
| 2007/0089557 A1 | 4/2007 | Solomon et al. | |
| 2007/0142969 A1 | 6/2007 | Devengenzo et al. | |
| 2008/0021440 A1 | 1/2008 | Solomon | |
| 2008/0087871 A1 | 4/2008 | Schena | |
| 2009/0229388 A1 | 9/2009 | Lee et al. | |
| 2011/0107866 A1 | 5/2011 | Oka et al. | |
| 2011/0137322 A1 | 6/2011 | Moll et al. | |
| 2013/0239392 A1 | 9/2013 | Solomon et al. | |
| 2013/0239735 A1 | 9/2013 | Solomon et al. | |
| 2013/0244820 A1 | 9/2013 | Solomon et al. | |
| 2014/0094824 A1 | 4/2014 | Cooper et al. | |
| 2015/0250549 A1 | 9/2015 | Solomon | |

FOREIGN PATENT DOCUMENTS

| | | |
|---|---|---|
| DE | 2819976 | 11/1979 |
| EP | 239409 | 9/1987 |
| EP | 0291292 | 11/1988 |
| EP | 0595291 | 5/1994 |
| FR | 2460762 | 1/1981 |
| FR | 2593106 | 3/1990 |
| FR | 2845889 | 2/2005 |
| GB | 2117732 | 10/1983 |
| JP | 7059788 A2 | 3/1995 |
| JP | 7136173 A2 | 5/1995 |
| WO | WO-9501757 | 1/1995 |

OTHER PUBLICATIONS

Extended European Search Report for Application No. EP10175715, dated May 24, 2012, 7 pages.

PCT/US05/32488 International Search Report, dated May 9, 2006, 4 pages.

PCT/US05/32488 Written Opinion of the International Search Authority, dated May 10, 2006, 7 pages.

Extended European Search Report for Application No. EP10175702, dated Jun. 13, 2013, 8 pages.

PCT/US06/62377 International Search Report and Written Opinion of the International Searching Authority, dated Jul. 16, 2008, 6 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Alexander, Arthur D. III, "Impacts of Telemation on Modern Society," Symposium on Theory and Practice of Robots and Manipulators, Centre for Mechanical Sciences 1st CISM IFToMM Symposium, Sep 5-8, 1973, pp. 121-136, vol. 2, Springer-Verlag.

Ben Gayed et al., "An Advanced Control Micromanipulator for Surgical Applications," Systems Science, 1987, pp. 123-134, vol. 13.

Guerrouad, Aicha el al., "SMOS: Stereotaxical Microtelemanipulator for Ocular Surgery," IEEE Engineering in Medicine and Biology Society 11th annual international conference, Nov. 9-12, 1989, pp. 879-880, vol. 3, IEEE.

NG, W.S. et al., "Robotic Surgery, A First-Hand Experience in Transurethral Resection of the Prostate," IEEE Engineering in Medicine and Biology, Mar. 1993, pp. 120-125, vol. 12—Issue I, IEEE.

Rininsland, Hermann; "ARTEMIS: A telemanipulator for cardiac surgery," European Journal of Cardio-Thoracic Surgery, vol. 16, Supplement 2, pp. S106-S111, Nov. 1999.

Rosheim, Mark E., "Robot Evolution: Development of Anthrobotics," Pub. John Wiley and Sons, Inc., New York, 1994, Chapter 2, pp. 37-156.

Belt Technologies, "Belt Technologies, Inc. Design Guide and Engineer's Reference for Metal Belts," 1999, 28 pages.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.

Extended European Search Report for Application No. 16179332.8, dated Jun. 22, 2017, 8 pages (017516-010200DIV3/EP).

\* cited by examiner

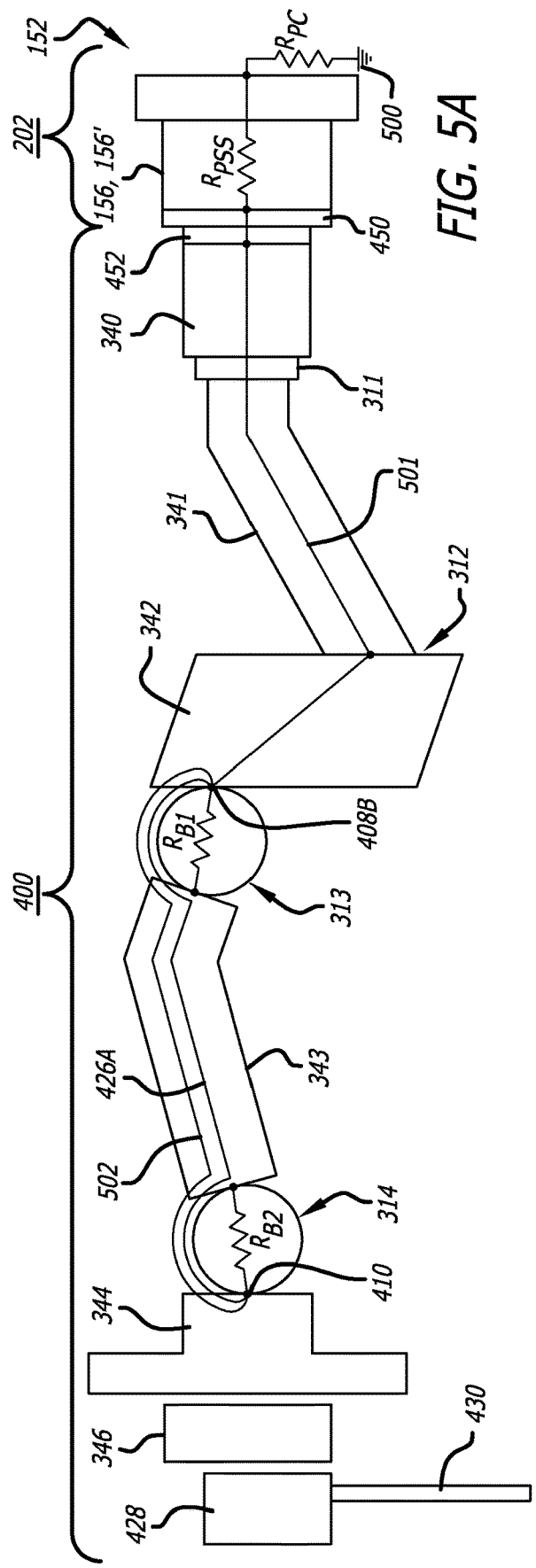
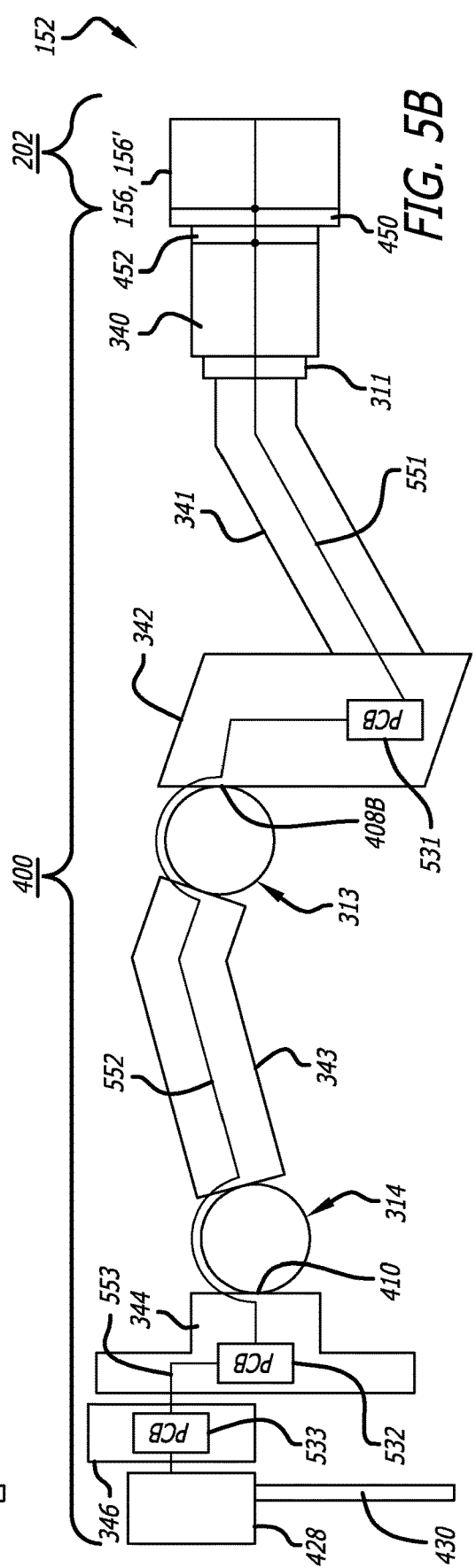
FIG. 5A
FIG. 5B

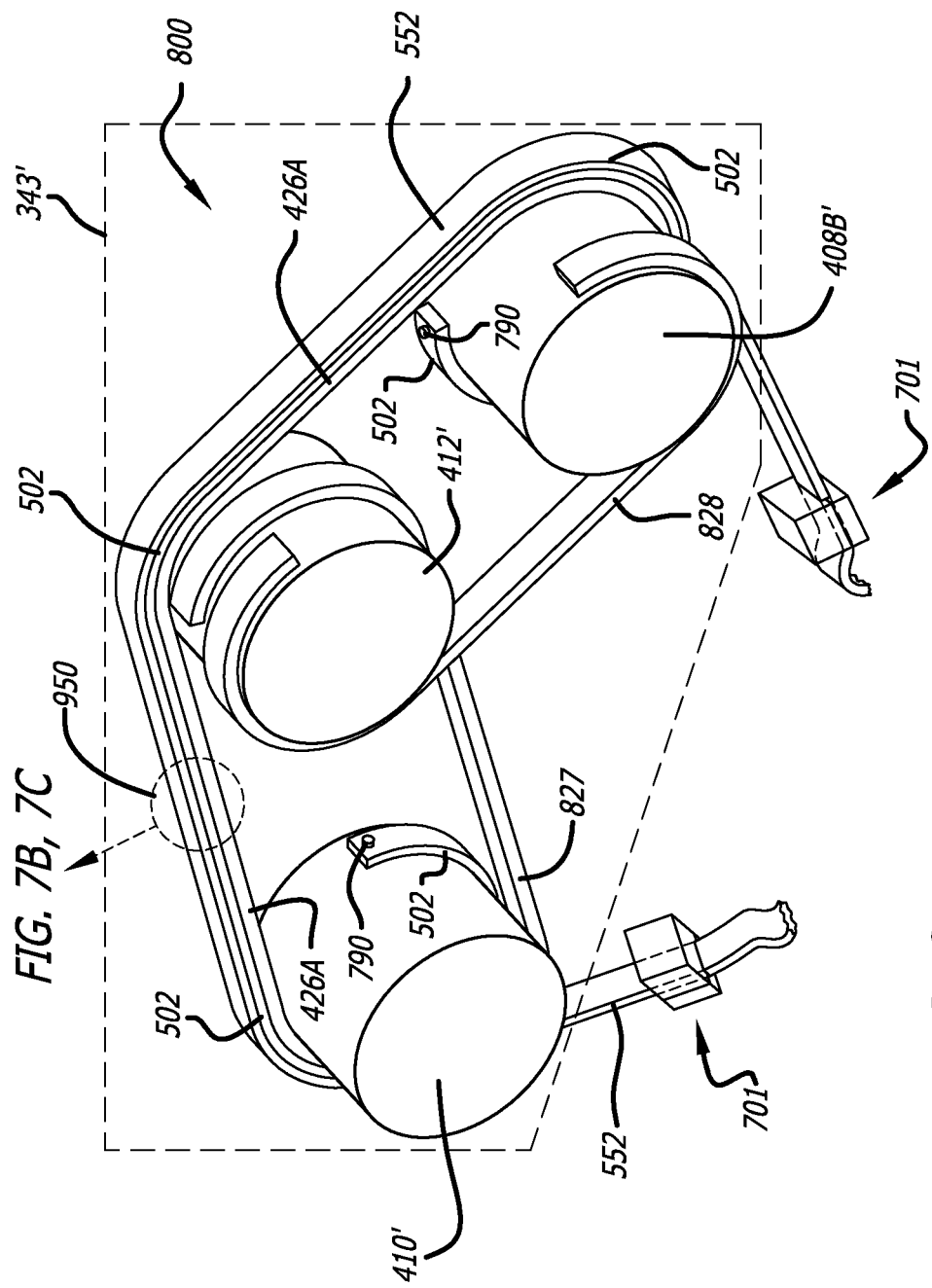

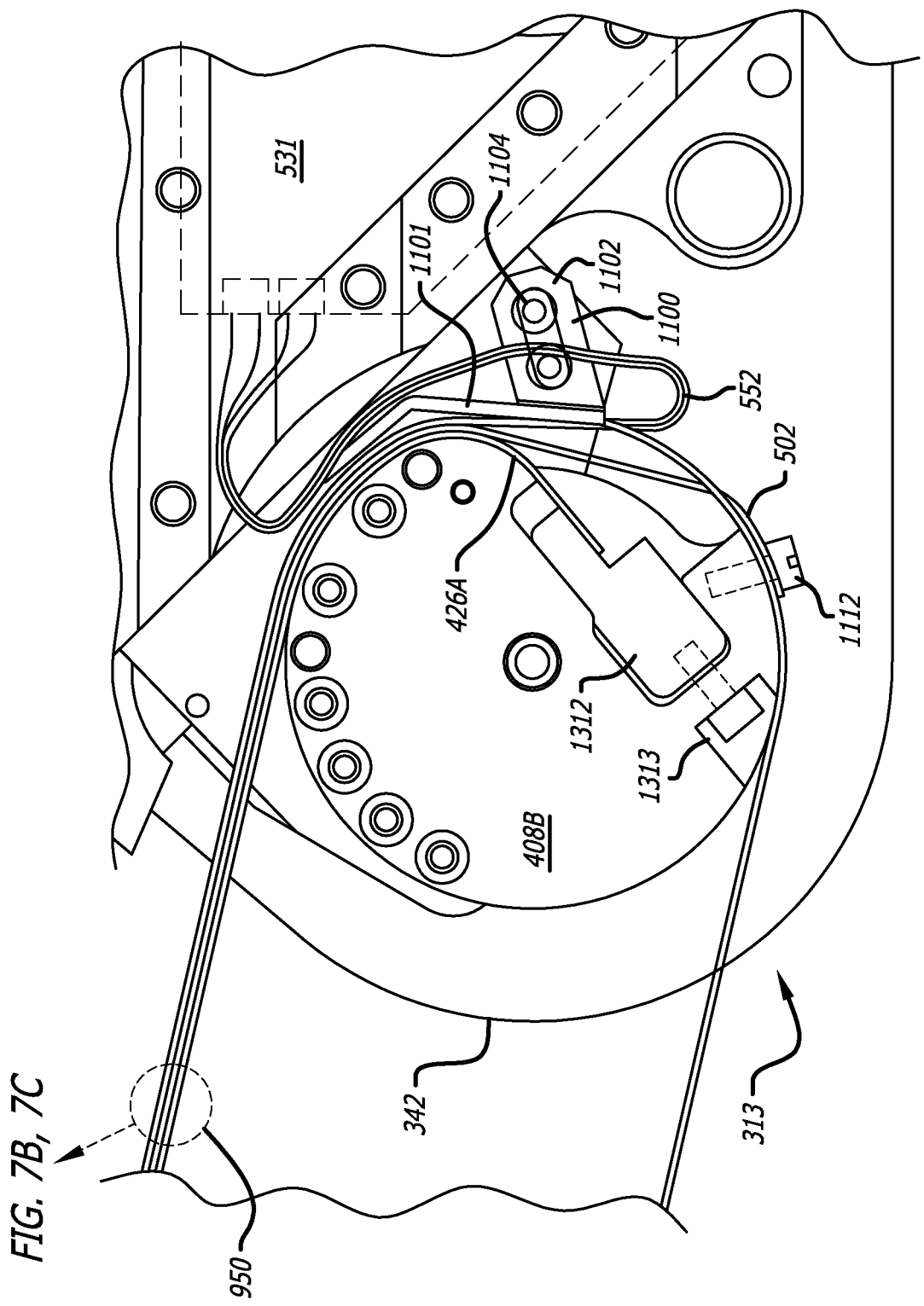

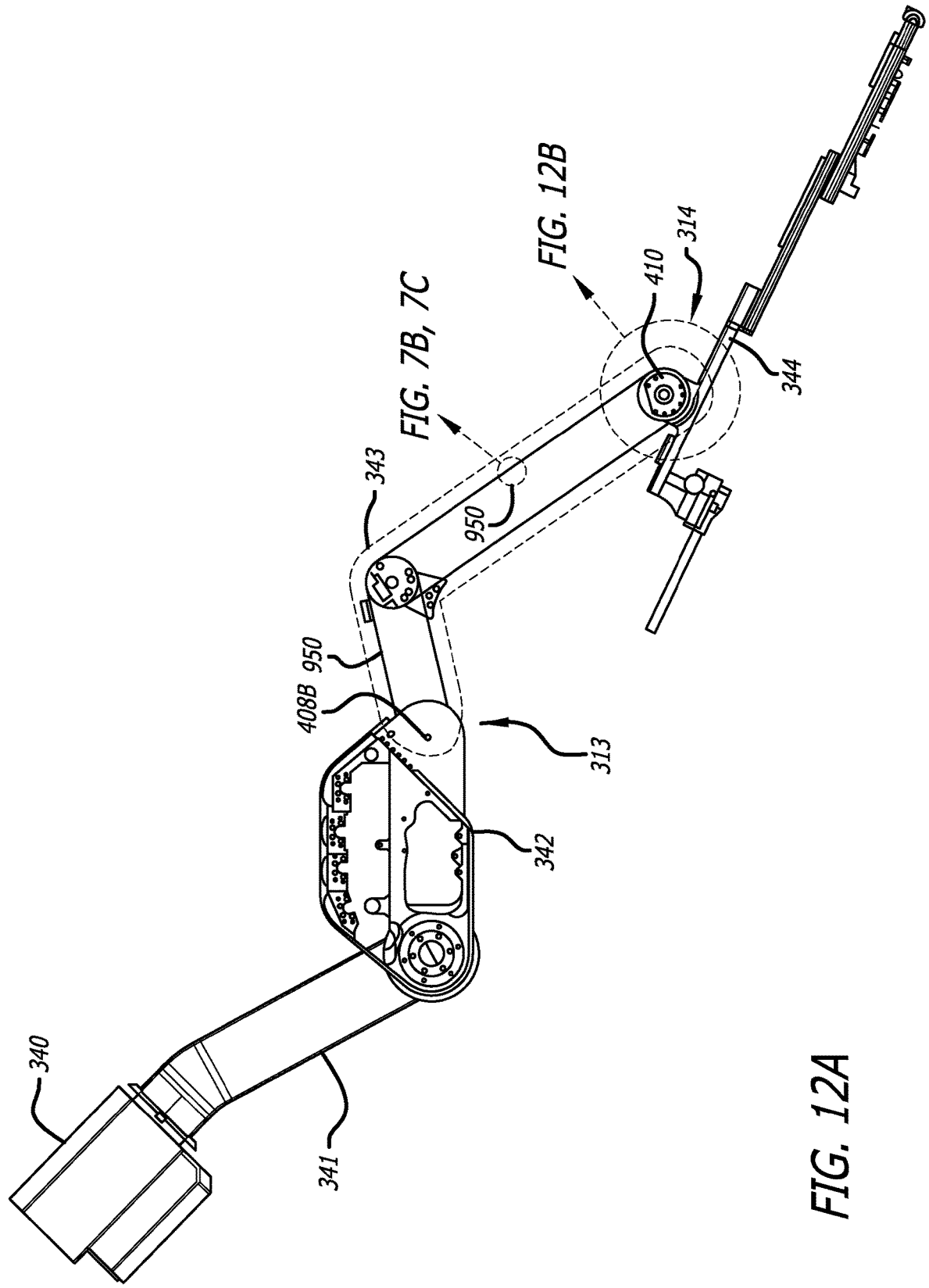

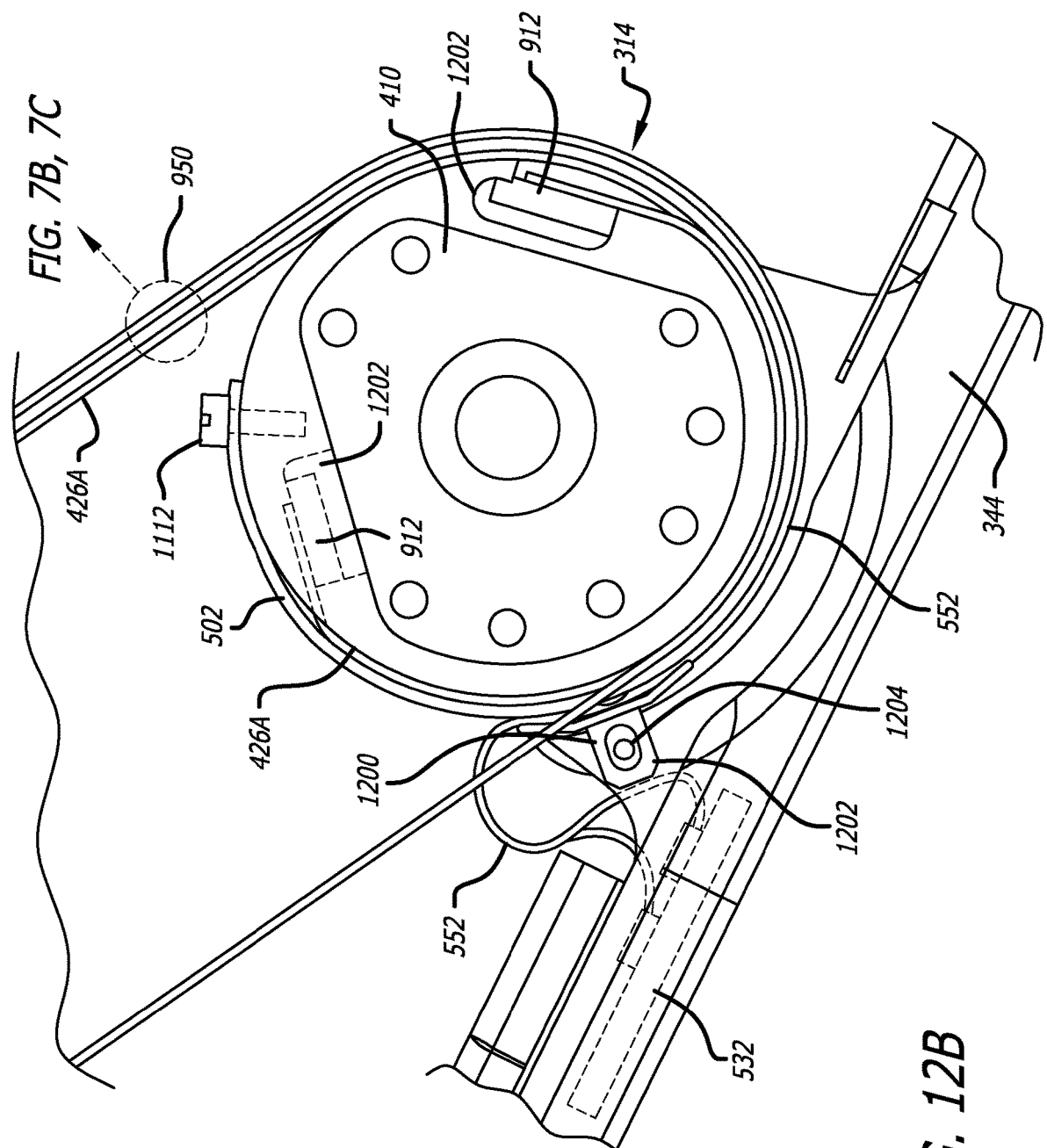

dance with the schematic of FIG. 5B,

ELECTRO-MECHANICAL STRAP STACK IN ROBOTIC ARMS

CROSS-REFERENCE TO RELATED APPLICATIONS

This non-provisional patent application claims the benefit of U.S. Provisional Patent Application No. 60/752,788, entitled "FLAT ELECTRICAL CONDUCTORS OVER PULLEYS IN A STRAP DRIVE-TRAIN OF A ROBOTIC SURGICAL ARM" filed by Todd R. Solomon on Dec. 21, 2005; and is also a continuation in part and claims the benefit of U.S. patent application Ser. No. 10/957,077, entitled "Offset Remote Center Manipulator for Robotic Surgery", filed on Sep. 30, 2004 by Thomas G. Cooper and Todd R. Solomon.

This non-provisional patent application also claims the benefit of and is related to U.S. Patent Application No. 60/752,514, entitled MULTI-PLY STRAP DRIVE-TRAIN FOR ROBOTIC SURGICAL ARM filed by Todd R. Solomon and Thomas G. Cooper on Dec. 20, 2005, which is hereby incorporated by reference.

FIELD

The embodiments of the invention relate generally to wiring power, ground, and signals through a surgical robotic arm. More particularly, the embodiments of the invention relate to electrical cable routing and chassis grounding of a surgical robotic arm.

BACKGROUND

Medical devices must comply with IEC601-1, which requires that all metal surfaces exposed to a patient or a hospital staff person must be electrically grounded. Moreover, the resistance to ground is required to be less than or equal to 200 milli-ohms ($10^{-3}$ ohms). It is desirable to meet this requirement in robotic surgical systems.

Additionally, there is often electrical cabling in a robotic surgical arm that may be subject to bending and chaffing around joints of motion. It is desirable to make electric cabling in a robotic surgical arm more reliable to avoid open signal lines and shorting of signal lines to ground.

BRIEF SUMMARY

The embodiments of the invention are summarized by the claims that follow below.

BRIEF DESCRIPTIONS OF THE DRAWINGS

FIG. 1 is a block diagram of a robotic surgery system to perform minimally invasive robotic surgical procedures using one or more robotic surgical arms with a strap drive-train.

FIG. 2 a perspective view of a robotic patient-side system of FIG. 1 with the one or more robotic surgical arms having the strap drive-train.

FIG. 5A is a schematic side view of chassis ground strapping in the robotic surgical arm.

FIG. 5B is a schematic side view of signal power, ground, and data/control cables in the robotic surgical arm.

FIG. 8 is a side perspective view of an exemplary three-strap system with an electromechanical strap stack that may be used in the third link.

FIGS. 11A-11B illustrate a schematic overview and a detailed magnified side view of the electromechanical strap stack at the third joint of the robotic surgical arm.

FIGS. 12A-12B illustrate a schematic overview and a detailed magnified side view of the electromechanical strap stack at the third joint of the robotic surgical arm.

Figure 1:
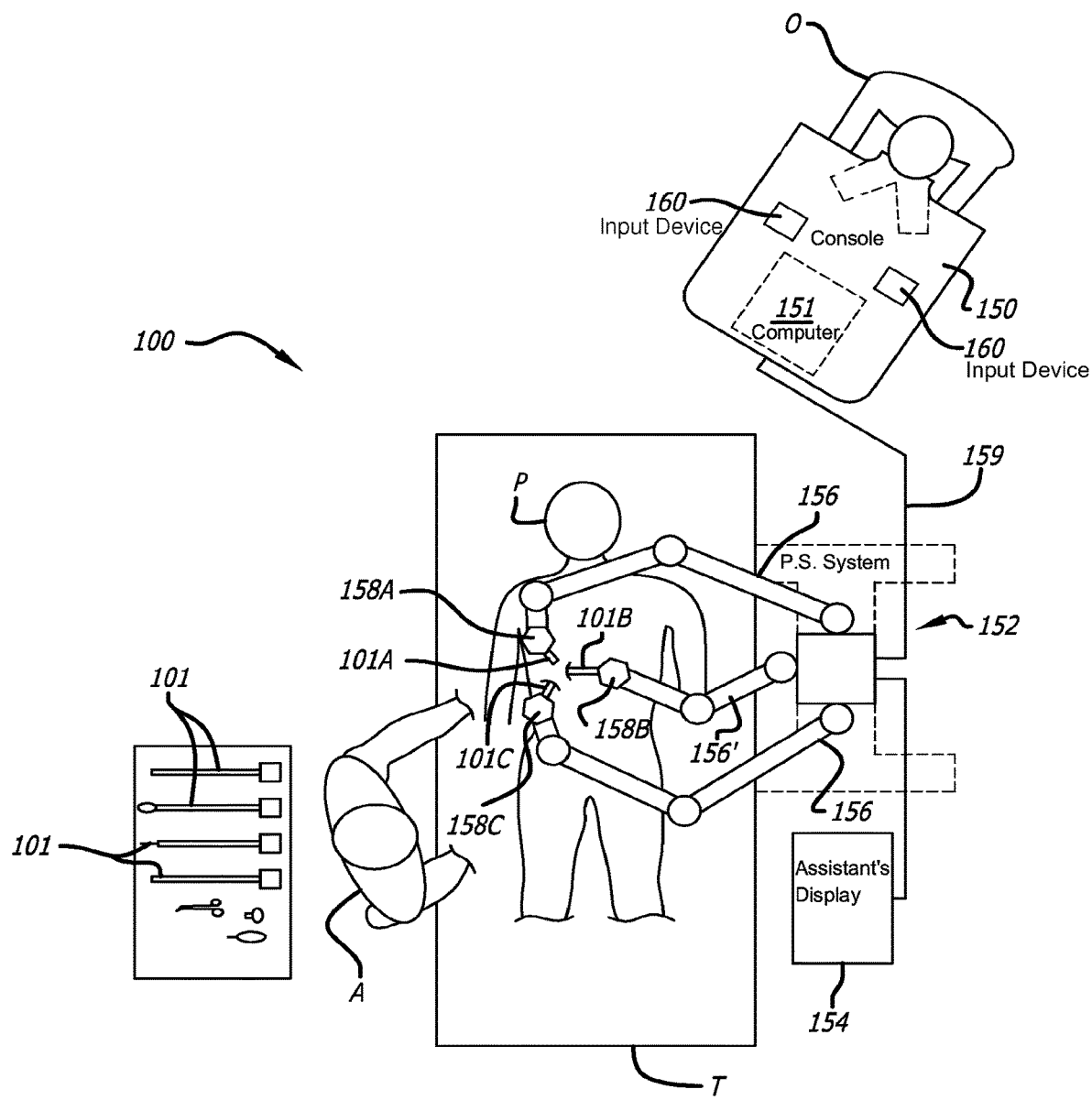

It will be appreciated that all the drawings of Figures provide for herein are for illustrative purposes only and do not necessarily reflect the actual shape, size, or dimensions of the elements being illustrated

DETAILED DESCRIPTION

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include a method, apparatus, and system for robotic surgical systems. In one embodiment of the invention a robotic surgical system is provided including flat electrical conductors over pulleys in a strap drive-train of a robotic surgical arm.

In one embodiment of the invention, a strap drive-train for use in a robotic surgical arm to enable movement of a linkage assembly of the robotic surgical arm is provided. The linkage assembly includes a plurality of links pivotally coupled in series together at a plurality of joints, respectively, for movement of the robotic surgical arm about a pitch axis. The strap drive-train includes a first driver pulley rigidly coupled to a link of the plurality of links and a second driver pulley rigidly coupled to another link of the plurality of links. The electro-mechanical strap stack includes at least one of a ground strap and an electrical cable strap in a stacked configuration with a drive strap, wherein the electro-mechanical strap stack is connected between the first driver pulley and the second driver pulley through a middle link.

In another embodiment of the invention, a robotic surgical arm is provided that includes a linkage assembly having a plurality of links pivotally coupled in series together at a plurality of joints, respectively, to provide an insertion axis for the robotic surgical arm. A strap drive-train is utilized to enable movement of the linkage assembly about a pitch axis. The strap drive-train includes an electro-mechanical strap stack coupled between a drive link and an instrument holder link of the plurality of links. The electro-mechanical strap stack includes at least one of a ground strap and an electrical cable strap in a stacked configuration with a drive strap.

In a further embodiment of the invention, a method for a robotic surgical arm is provided. The method includes operations comprising: pitching a linkage assembly that includes a plurality of links coupled in series together to provide an insertion axis for the robotic surgical arm; and enabling movement of the linkage assembly about a pitch axis with a strap drive-train coupled thereto that utilizes an electro-mechanical strap stack coupled between a drive link and an instrument holder link, wherein the electro-mechanical strap stack includes at least one of a ground strap and an electrical cable strap in a stacked configuration with a drive strap.

In an additional embodiment of the invention, a strap drive-train for use in a robotic surgical arm to enable movement of a linkage assembly of the robotic surgical arm is provided. The linkage assembly includes a plurality of links pivotally coupled in series together at a plurality of joints, respectively, for movement of the robotic surgical arm about a pitch axis. The strap drive-train includes a first driver pulley rigidly coupled to a drive link of the plurality of links, a second driver pulley rigidly coupled to an instrument holder link of the plurality of links, and an electro-mechanical strap stack. The electro-mechanical strap stack includes a ground strap having a conductive material and a flexible electrical cable strap having one or more flexible electrical signal lines. The ground strap and the flexible electrical cable strap are stacked and arranged in parallel configuration with a drive strap. The electro-mechanical strap stack is connected between the first driver pulley and the second driver pulley through a middle link located between the drive link and the instrument holder link.

Robotic Surgical System

Referring now to FIG. 1, a block diagram of a robotic surgery system 100 is illustrated to perform minimally invasive robotic surgical procedures using one or more robotic surgical arms with a strap drive. Robotic surgery generally involves the use of a robot manipulator that has multiple robotic manipulator arms. One or more of the robotic manipulator arms 158 often support a surgical tool 101A, 101C which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like).

At least one of the robotic manipulator arms 158 (e.g., the center robotic manipulator arm 158B) may be used to support a stereo or three dimensional surgical image capture device 101B such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C by means of one or more control cables 159, effecting movement of the instruments using a robotic patient-side system 152 (also referred to as a patient-side cart). The robotic patient-side system 152 has one or more robotic surgical arms 158 with the strap drive. Typically, the robotic patient-side system 152 includes at least three robotic manipulator arms 158A-C supported by linkages 156, 156', with a central robotic surgical arm 158B supporting an endoscopic camera 101B and the robotic surgical arms 158A, 158C to the left and right of center supporting tissue manipulation tools 101A, 101C.

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The actively driven portion of the robotic patient-side system 152 is generally referred to herein as the robotic surgical arms or alternatively to robotic surgical manipulators. The positioning portion of the robotic patient-side system 152 that is in a fixed configuration during surgery may be referred to as "set up arms" 156, 156' with positioning linkage and/or "set-up joints". In an alternate embodiment of the invention, the robotic patient-side system 152 may be replaced by set up arms that couple at one end to left and right sides of the operating table T. The three robotic manipulator arms 158A-C may then be coupled to the opposite end of the set-up arms to ground to the table T.

For convenience in terminology, manipulators such as robotic surgical arms 158A and 158C actuating the tissue affecting surgical tools 101A and 101C are generally referred to herein as a PSM (patient-side manipulators). The robotic surgical arm 158B controlling an image capture or data acquisition device, such as the endoscopic camera 101B, is generally referred to herein as an ECM (endoscopic camera manipulator). Note that such telesurgical robotic manipulators may optionally actuate, maneuver and control a wide variety of instruments, tools and devices useful in surgery which with the tissue affecting surgical tools 101A and 101C and the endoscopic camera 101B may generally be referred to by the reference number 101.

An assistant A may assist in pre-positioning of the robotic patient-side system 152 relative to patient P as well as swapping tools or instruments 101 for alternative tool structures, and the like, while viewing the internal surgical site via an assistant's display 154.

Figure 2:
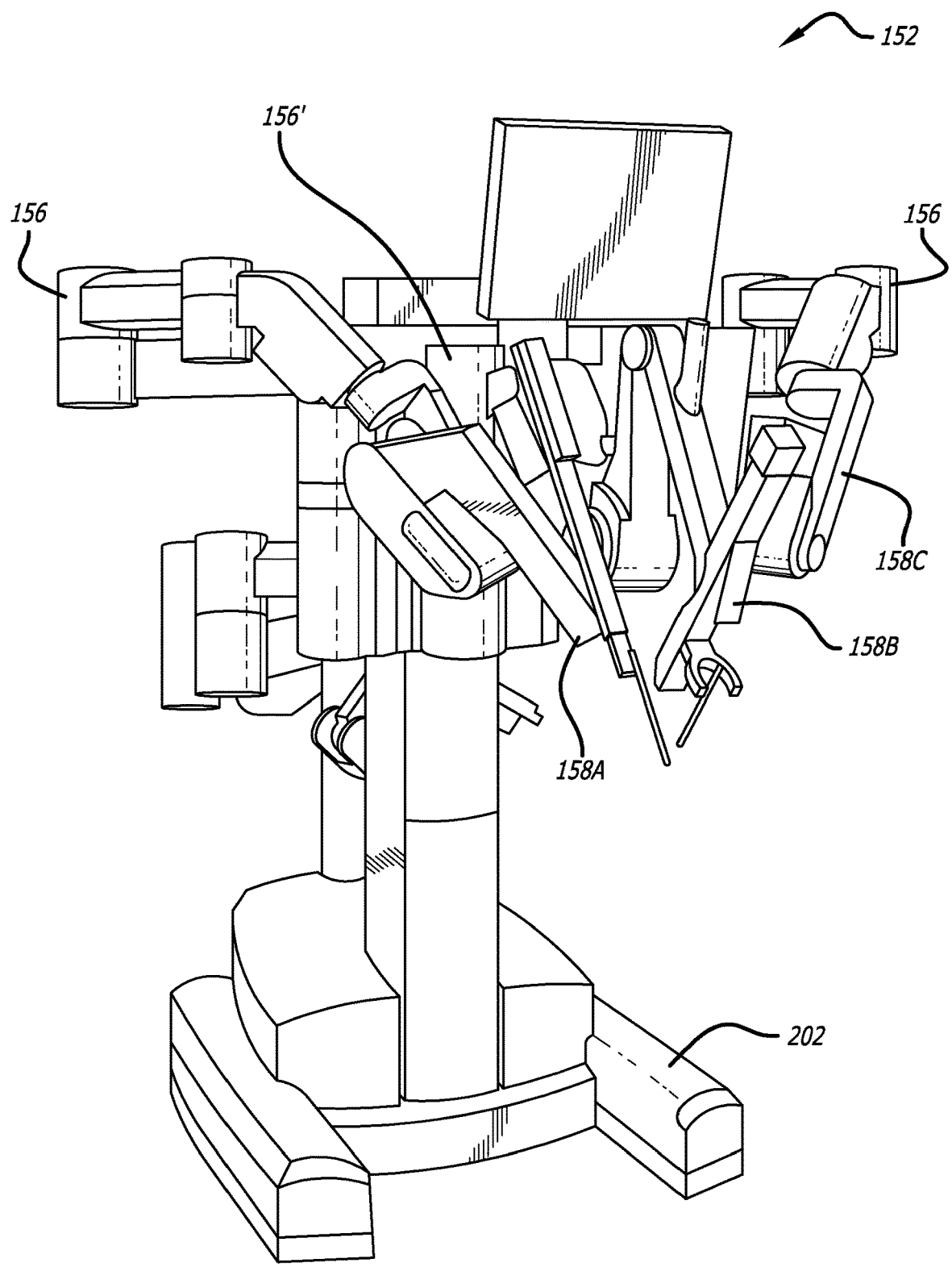

Referring now to FIG. 2, a perspective view of the robotic patient-side system 152 is illustrated. The robotic patient-side system 152 has one or more robotic surgical arms (a.k.a., robotic surgical manipulators) 158A-158C with the strap drive system. The robotic surgical arms 158A and 158C are for coupling to robotic surgical tools 101A and 101C. The robotic surgical arm 158B is for coupling to an endoscopic camera 101B. The robotic patient-side system 152 further includes a base 202 from which the robotic surgical instruments 101 may be supported. More specifically, the robotic surgical instruments 101 are each supported by the positioning linkage 156 and the robotic surgical arms 158. The linkage structures may optionally be covered by protective covers or not to minimize the inertia that is manipulated by the servomechanism and the overall weight of robotic patient-side system 152.

The robotic patient-side system 152 generally has dimensions suitable for transporting between operating rooms. It typically can fit through standard operating room doors and onto standard hospital elevators. The robotic patient-side system 152 may have a weight and a wheel (or other transportation) system that allows the cart to be positioned adjacent an operating table by a single attendant. The robotic patient-side system 152 may be sufficiently stable during transport to avoid tipping, and to easily withstand overturning moments that may be imposed at the ends of the robotic surgical arms during use.

Robotic Surgical Arms with Multiple Control Straps

Figure 3:
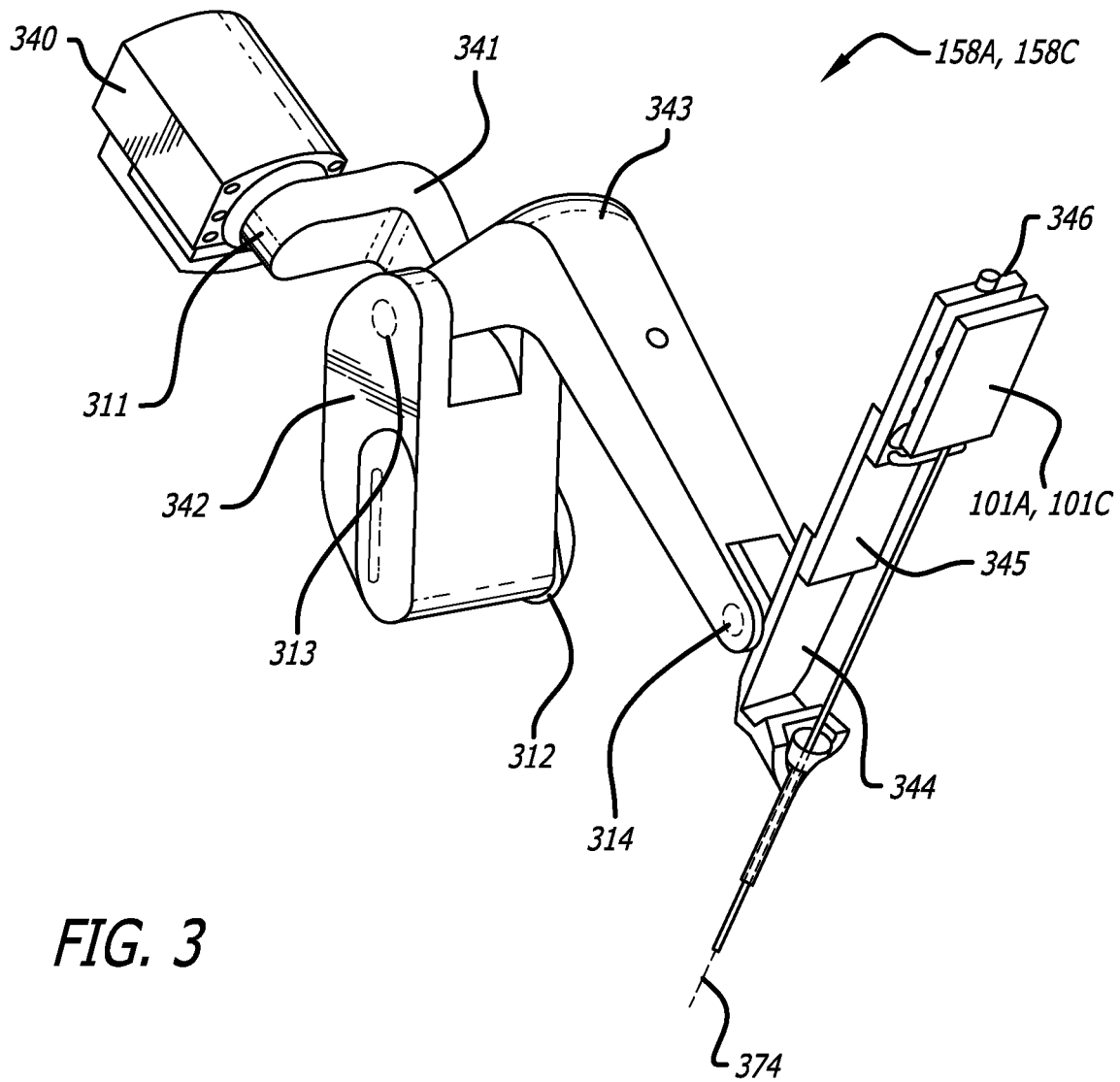
FIG. 3 is a perspective view of a surgical manipulator or robotic surgical arm.

Referring now to FIG. 3, a perspective view of the robotic surgical arms 158A and 158C is illustrated. As discussed previously, the robotic surgical arms 158A and 158C are for coupling to robotic surgical tools 101A and 101C, respectively. The robotic surgical arms 158A and 158C each include serial links 341-344 pivotally coupled in series at joints 312-314 near respective ends of the links. The first link (Link 1) 341 is pivotally coupled to a drive mount 340 at a first joint 311 near a first end and the second link (Link 2) 342 at the second joint 312 near a second end. The third link (Link 3) 343 is pivotally coupled to the second link 342 at the third joint 313 near a first end and pivotally coupled to the fourth link (Link 4) 344 at the fourth joint 314 near a second end. Generally, the fourth link 344 is substantially parallel to the insertion axis 374 of the robotic surgical tool. A fifth link (Link 5) 345 is slidingly coupled to the fourth link 344. A sixth link (Link 6) 346 is slidingly coupled to the fifth link 345. Various types of surgical tools 101A, 101C couple to the sixth link 346.

The robotic surgical arms 158A and 158C further include a mounting base 340 that allows them to be mounted and supported by set-up arms/joints 156 of a cart mount, ceiling mount, floor/pedestal mount, or other mounting surface of a patient side system 152. The mounting base 340 is pivotally coupled to the first link 341 to yaw the robotic surgical arm about a yaw axis.

The third link 343 has a bend with respect to the pitch axis that is offset from center. The bend in the third link allows the links 342-344 to be brought more closely together and provide a greater range of pitch in the robotic arm. The bend may be formed at different angles depending upon the lengths and shapes of the other links. With the bend, the third link is shaped somewhat like a hockey stick. The first link 341 also has a bend with respect to the pitch axis. Thus, the third link 343 may alternately be referred to as a bent link, the main bent link, or a hockey stick shaped link. With no yaw, the second link 342 provides a vertical motion in the third link 343. Additionally, the second link 342 may house the motor to drive the linkage of the arm. Thus, the second link 342 may also be referred to as the vertical link or the drive link. As the fourth link 344 typically slidingly holds the robotic surgical tool 101A, 101C or the endoscopic camera through the fifth and sixth links, the fourth link may also be referred to as the instrument holder link.

Figure 4:
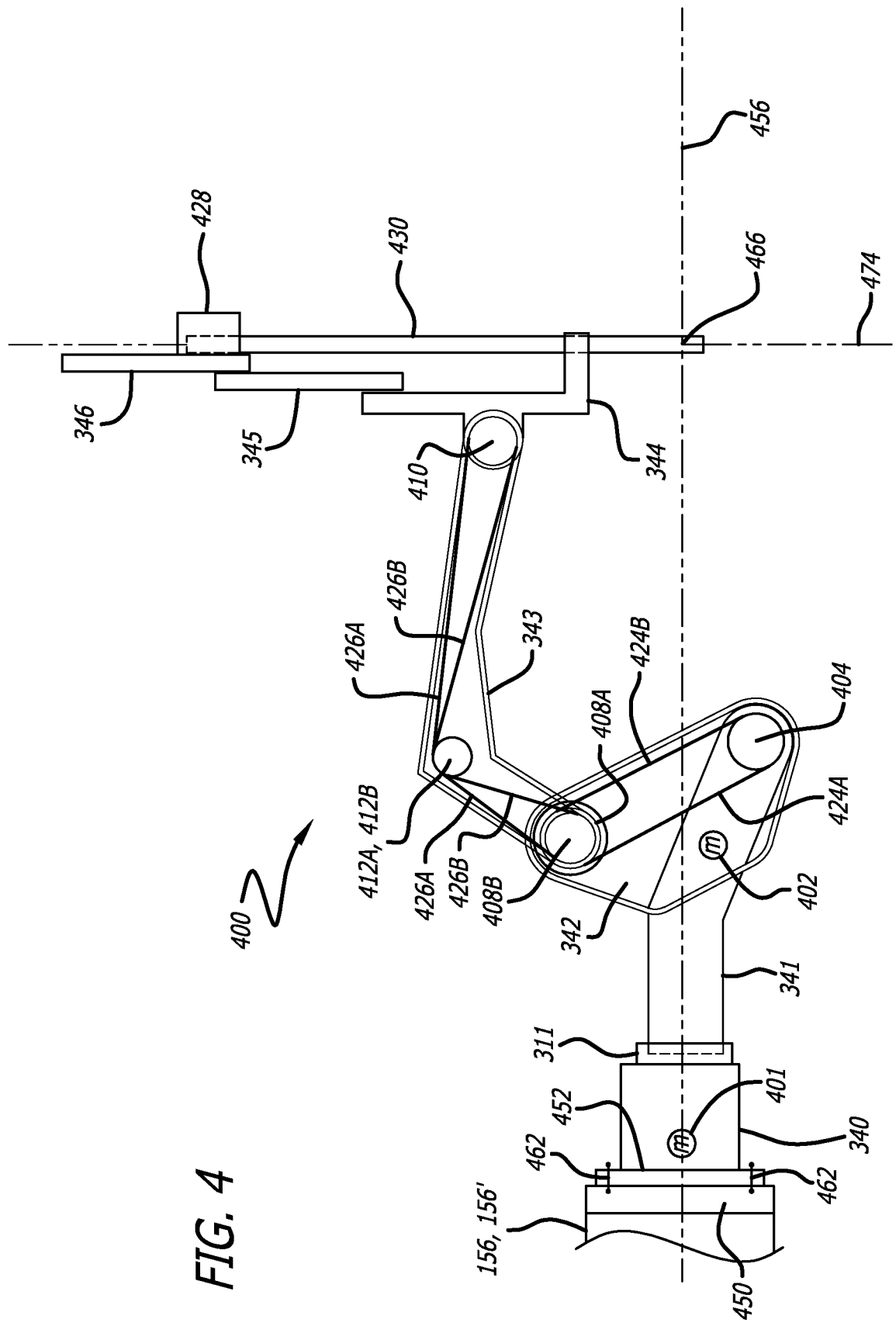
FIG. 4 is a schematic side view of one embodiment of a multi-strap drive-train including an electromechanical strap stack.

Referring now to FIG. 4, a schematic diagram of the strap drive-train of an exemplary embodiment of a robotic surgical arm 400 is illustrated. The strap drive-train of the robotic surgical arm 400 may be used in the structure of the arms 158A-158C illustrated in FIGS. 1, 2, and 3 in one embodiment of the invention. The strap drive-train of the robotic surgical arm 400 drives the weight or load of the robotic surgical arm itself from the links, joints, pulleys, cables, straps, etc. and the load that may be placed on it by the surgical tool in the surgical site. Without the strap drive-train, the robotic surgical arm would collapse and a remote center point 466 would not be maintained.

While the robotic surgical arm 400 includes links and joints as described herein, the strap drive-train of the robotic surgical arm 400 includes six pulleys 404, 408A, 408B, 410, 412A, 412B and four straps 424A, 424B, 426A, 426B in one embodiment of the invention. The six pulleys 404, 408A, 408B, 410, 412A, 412B and four straps 424A, 424B, 426A, 426B are configured with the links and joints of the robotic surgical arm 400 to constrain the motion of the shaft 430 of the surgical tool 428 or endoscopic camera relative to the center of rotation 466.

In the second link 342, straps 424A-424B are coupled between drive pulleys 404 and 408A. In the third link 343, the straps 426A-426B are coupled between drive pulleys 408B, 410 and ride over the idler pulleys 412A, 412B, respectively, in one embodiment of the invention. At the second joint, pulley 404 is rigidly coupled to the first link 341. At the third joint 313, pulley 408A is rigidly coupled to the third link 343. At the third joint 313, pulley 408B is rigidly coupled to the second link 342. At the fourth joint 314, pulley 410 is rigidly coupled to the fourth link 344.

The mounting base 340 includes a motor 301 to yaw the robotic surgical arm 400 about the axis 456.

In FIG. 4, the mounting base 340 of the surgical robotic surgical arm 400 includes electrical and mechanical connectors 452 to mate with electrical and mechanical connectors 450 in a base support coupled to the set up arm 156,156'. Additionally, fasteners 462 (such as bolts) may be used to rigidly couple the robotic surgical arm 400 to the set up arm 156,156'. Alternatively, a lever arm may be used to lock and unlock the arm 400 from the arms 156,156' to quickly mount and dismount the robotic surgical arm from the patient side system.

Ground Straps for Chassis Ground

As discussed previously, all metal surfaces that are exposed to a patient or a hospital staff member should be electrically grounded with a ground resistance of less than or equal to 200 milli-ohms to meet the standard set forth in International Electrotechnical Commission Publication 601-1 (the "IEC standard"). In the robotic surgical arm 158, 400 there are a number of joints 313, 314 with bearings that increase the resistance of chassis ground in the linkage. Without ground straps around the joints, the IEC standard would not be met. However, with typical ground cabling around the joints, the ground cabling moves and bends with the linkage and may cause fatigue. Moreover, as slack is required to facilitate the joint movement, the extra cable length increases the resistance to chassis ground. Thus, it is desirable to improve upon the ground strapping typically used around the joints of a robotic arm.

As discussed previously, straps and pulleys are used to control the mechanical movement of the links in the robotic arm. In particular, drive strap 426A is used to mechanically couple pulleys 410 and 408B together. Additionally, pulley 410 is rigidly coupled to the fourth link 344 so as to make a mechanical and electrical connection thereto. Pulley 408B is rigidly coupled to the second link 342 so as to make a mechanical and electrical connection thereto. In one embodiment of the invention, the straps, including strap 426A, are formed of one or more layers of metal. The metal strap 426A is wrapped around the pulleys 410, 408B and has metal ends welded thereto which are in turn coupled to the pulleys 410, 408B so as to make a sufficient ground strap between the second link 342 and the fourth link 344. This is schematically shown in FIG. 5A.

Referring now to FIG. 5A, an exemplary schematic diagram of the resistances seen between chassis ground 500 and an external metal portion of the robotic surgical arm, such as the fourth link 344 is shown. The patient side cart system 152 sees a power cord resistance $R_{PC}$ to ground at the electrical power outlet. In the patient side cart 152, there is a patient side cart resistance $R_{PSS}$ to the electrical interface 450 of the set-up joints 156, 156'. That is, the base portion 202 of the patient side system 152 has a resistance $R_{PSS}$ to the electrical interface 450. The robotic surgical arm 400 also has a resistance total associated with it from the electrical interface 452 to the exposed metal surfaces in the linkage 344. Included in the total resistance for the robotic surgical arm 400 is a first bearing resistance ($R_{B1}$) associated with the bearings at the third joint 313 and a second bearing resistance $R_{B2}$ at the fourth joint 314.

As discussed previously, the metal drive strap 426A may be used as a ground strap and couples the second link 342 to the fourth link 344 as schematically illustrated in FIG. 5A.

At the interface connector 452, a ground cable 501 extends from the electrical interface 452 through the base mount 340, the first joint 311, through the first link 341, and couples to the chassis of the link 342.

With pulley 408B electrically coupled to the second link 342, the strap 426A has one end coupled thereto that wraps around the joint 313 in parallel with the bearing $R_{B1}$ resistance of the joint. The strap 426A travels through the third link 343, wraps around the fourth joint 314 and couples to the pulley 410 illustrated by a point in FIG. 5A which is also coupled to the fourth link 344. In this manner, the metal drive strap 426A acts as a grounding strap wrapping around the pulleys 408B and 410 and the joints 313, 314, respectively to be in parallel with the bearing resistances $R_{B1}$ and $R_{B2}$.

In addition to the metal drive strap 426A, a ground strap 502 is stacked on top of the metal strap 426A to provide further ground strapping between the second link 342 and the fourth link 344 to further lower the chassis ground resistance around the third link 343. In a preferred embodiment of the invention, the ground strap 502 consists of one or more layers of beryllium copper metal straps such as to stack on top of the stainless steel multi-ply drive straps 426A. The ground strap 502 is also wrapped around the pulleys 408B and 410 to control bending stresses therein and improve reliability over that of conventional standard ground cable wires. Alternatively, other conductive materials could be used, such as other metals or alloys, or woven flat ground straps.

The total budget allowed by the International Electrotechnical Commission (IEC) Publication 601-1 for a medical device that comes in contact with patients is less than or equal to 200 milli-ohm. This resistance is from the ground pin at the proximal end of the system's power plug (that plugs into the wall) to any exposed metal surface on the robotic surgical system (see FIG. 2) that can be touched by the patient or operating room personnel within the vicinity of the patient. The resistance in a robotic surgical system may be budgeted as follows in one embodiment of the invention:

1) Power cord, end to end: 100 milli-ohms
2) From the proximal end of base 202, where the power cord plugs into it, to the distal end of the positioning linkage 156 or 156', where the robotic surgical arms 158A, B or C mount: 40 milli-ohms
3) Robotic surgical arm, from proximal end to an exposed metal surface: 60 milli-ohms Total: 200 milli-ohms The ground strapping 502 in parallel with the metal strap 426A provides a sufficient reduction in chassis ground resistance between the second link 342 and the fourth link 344 over the resistance in the joints and the third link 343 to readily meet the goal of sixty milli-ohms of resistance in chassis ground of the robotic surgical arm from a proximal end at the interface 452 to a distal end to an exposed metal surface, such as the fourth link 344.

In addition to lowering the resistance in chassis ground by using ground strapping; signal power, signal ground, and signal control/data signal lines are routed though the robotic surgical arm 400.

Flex Cables for Signal Ground, Power, and Control/Data

Referring now to FIG. 5B, a schematic diagram of the signal power, signal ground, and the control/data signal lines is illustrated. Signal power, signal ground and control/data signal lines are coupled to the electrical interface 450 of the set-up joint 156, 156'. With the robotic surgical arm 400 coupled to the set-up joint, its interface 452 receives the signal power, signal ground and control/data signals. The arm 400 includes cabling 551, 552, and 553 to couple signal power, signal ground and control/data signals to printed circuit boards (PCBs) 531-533, respectively. The first cable 551 couples power ground control data signals from the interface 452 through the first link 341 to the first printed circuit board 531 in the second link 342. The second cabling 552 couples power ground and controlled/data signals from the first PCB 531 through the third link 343 to the second PCB 532 in the fourth link 344. The third cabling 553 couples power ground control/data signals from the second printed circuit board 552 to the third printed circuit board 533 in the sixth link 346. The electrical interface of the robotic tool 428 couples to receive power ground and control signals from the third printed circuit board 533.

The cabling 552 may include one or more flat flexible signal cables that are wrapped around the joints 313 and 314 between links 342 and 343, and links 343 and 344. Accordingly, the cabling may be referred to as flat flexible signal cabling 552 (alternatively referred to as electrical cable strap; electrical cabling; flat flex cables; or flat flexible signal cabling). The flat flexible signal cabling 552 is stacked under or on top of the ground strapping 502 that is turn stacked on top of the drive strap 426A in the third link 343. The ends of the flat flexible signal cabling 552 couple to the first PCB 531 and the second PCB 532.

For electric machinery in general, it is often desirable to route electrical wiring through a manipulated arm. It is also often desirable to have high cycle life for equipment reliability. Thus, the embodiments of the invention are applicable to any flat electrical conductor that would route through an electric machine that has rotary joints that move. The flat electrical conductor could be, but is not limited to, a typical ribbon cable, a flat flex cable, a flex circuit, or a woven or solid flat piece of metal that is used as an electrical conductor (such as a ground strap).

By wrapping a flat electrical conductor around pulleys, the bend radius of the conductor will approximate the radius of the pulleys. The pulley supports the conductor and prevents its bend radius from being any smaller than the pulley radius. The larger the bend radius, the less the bending stresses are, and typically, the conductor will have a longer cycle life. Therefore, using large pulleys around which to wrap these conductors will typically increase the cycle life.

Stacked Strapping System

As previously mentioned, the ground strapping may stack on top of a drive strap. Additionally, signal cabling may stack under or on top of the ground strapping.

Figure 6:
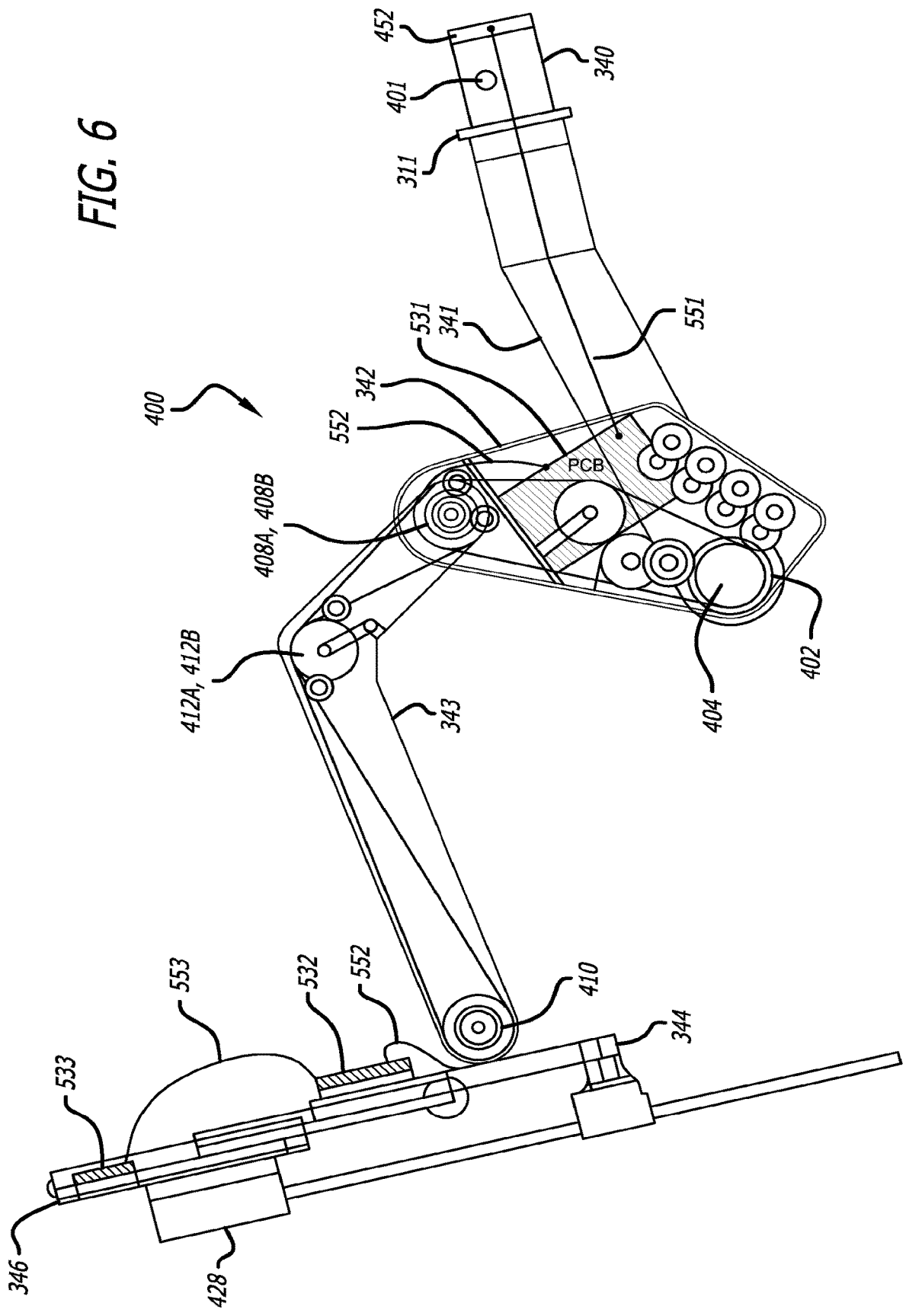
FIG. 6 is a schematic diagram of the flexible signal cabling routing through the robotic surgical arm in accordance with the schematic of FIG. 5B.

Referring now to FIG. 6, a side view of the linkage of the robotic surgical arm 400 is illustrated with the power ground and control/data signal cabling. As illustrated in FIG. 6, the cabling 551 couples between the control board (the first PCB) 531 and the electrical interface 452 at the mount 340. The cabling 551 travels through the center of the first linkage 341 and then couples to the control board 531. The control board 531 may be utilized to control the seven axes of movement of the robotical surgical arm 400. Additionally, sensor feedback may be processed by the control board 531 and coupled back to the surgeon's console 150.

Figure 7B:
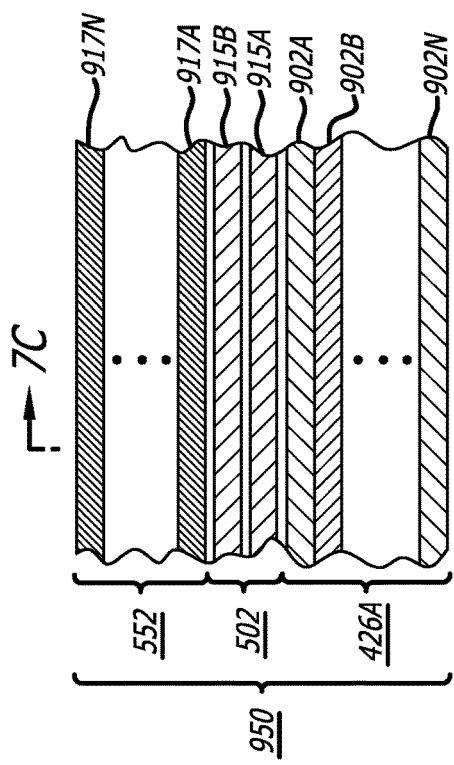
FIGS. 7B-7C are side and cross-sectional views of an exemplary electromechanical strap stack that may be used in the third link.
Figure 7C:
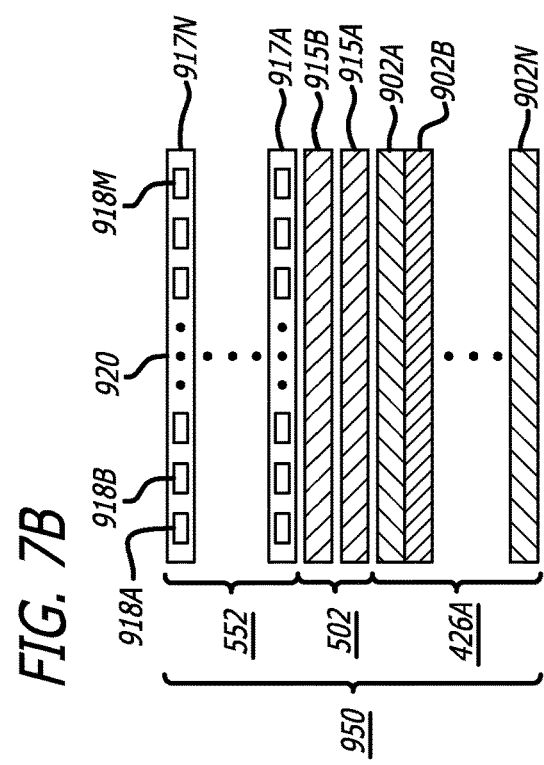
Figure 7A:
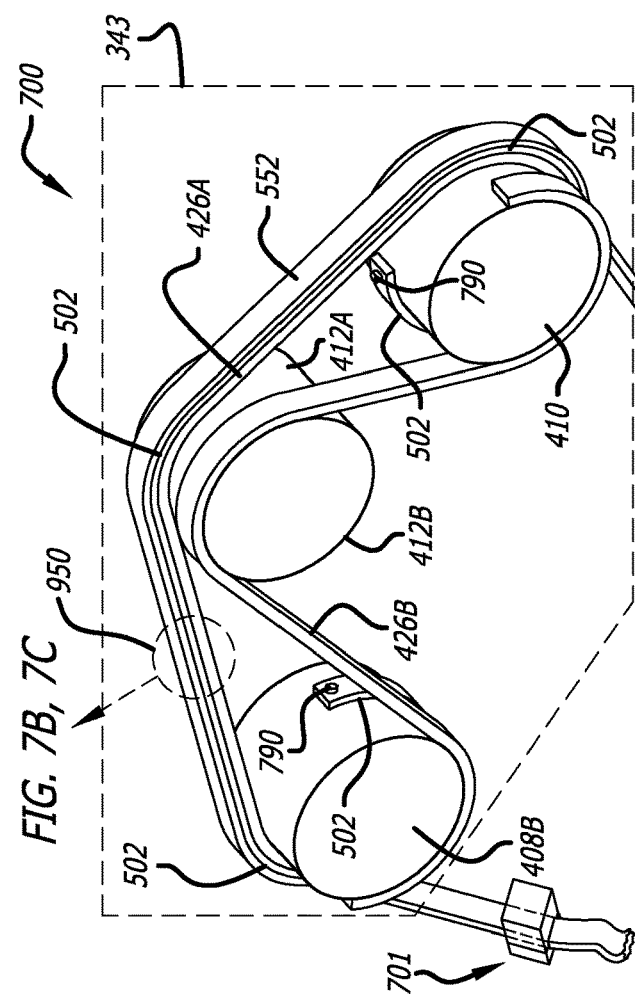
FIG. 7A is a side perspective view of an exemplary two-strap system with an electromechanical strap stack that may be used in the third link.

Referring now to FIGS. 6, 7A, and 8, cabling 552 couples at one end to the control board 531, wraps around onto the pulley 408B' (pulley 408B in the system 700) and travels along the metal drive strap 426A over the idler pulley 412', as the case may be with the three strap drive system 800, (or over the idler pulley 412A, as the case may be with the two strap drive system 700), and continues along the metal strap 426A and wraps around pulley 410' (pulley 410 in the system 700) and couples at the opposite end to the interface board 532. Near each end of the cabling 552, there is a bracket and clamp arrangement 701 to provide some slack in the cabling 552 before coupling to the respective printed circuit boards 532, 552.

The third cabling 553 couples at one end to the interface board 532 and at an opposite end to the tool interface board 533. The interface board 532 is an intermediate interfacing board between the tool interface board 533 and the control board 531. As discussed previously, the tool interface board 533 interfaces to the electronics of the robotic surgical tool 428. The control board 531 in particular controls the yaw motor 401 and the pitch motor 402.

Referring now to FIG. 7A, a perspective view of a two-strap drive system 700 used in a third link 343 is illustrated. The system 700 includes the two drive straps 426A-426B, the joint drive pulleys 408B, 410, and the idler pulleys 412A-412B for each respective strap 426A-426B. Each of the straps partially wraps around each pulley side-by-side over a wrap angle with the ends of the straps being rigidly coupled to the joint pulleys 408B, 410 so that no backlash occurs. The two straps 426A-426B are partially wrapped around the joint pulleys so as to move in opposite directions when the links are moved. That is, the ends of strap 426A are wrapped around each joint pulley in an opposite direction than how the ends of strap 426B are wrapped. Even though the two straps 426A-426B are routed side by side in the link housing, effectively they act as one continuous loop between the joint pulleys. However, the straps may be used as the pulleys pivot less than three hundred sixty degrees.

Because the third link (Link 3) 343 has a bend in it (i.e.—hockey-stick shaped), each strap 426A-426B wraps around it's own respective idler pulley 412A-412B, because the belts rotate in opposite directions about them. The idler pulleys 412A, 412B allow the straps 426A, 426B to navigate around the bend in the third link 343. In one embodiment of the invention, the idler pulleys are also used to tension the straps as discussed the related application Ser. No. 60/752,514 previously incorporated by reference. Otherwise, the idler pulleys are passive idlers.

The system 700 may be advantageous for single-ply drive straps or mechanical cables, as it requires only two drive straps. However in a number of embodiments of the invention, the drive straps are formed of a plurality of layers or plies of material. In a preferred embodiment of the invention, each of the drive straps includes a plurality of metal layers or plies. The plurality of layers or plies provides a safety redundancy over that of a single cable or single ply drive strap or belt. If any single ply breaks in a multi-ply drive strap due to a manufacturing defect, fatigue, or overload for example, the remaining plies prevent the robotic surgical arm from collapsing.

Figure 7D:
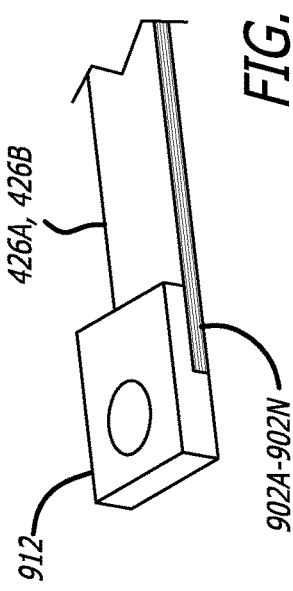
FIG. 7D is a perspective view of an end portion of a metal drive strap.

Referring now to FIG. 7D, a cut-away side view of drive strap 426A is illustrated. The drive strap 426A includes a plurality of metal layers or plies 902A-902N each having the same width and thickness. The plurality of metal layers or plies 902A-902N are stacked one on top of the other and may jointly be referred to by reference number 902. In one embodiment of the invention, each metal layer 902A-902N is steel. Alternatively, other types of metal, alloy, or other materials can be used. There is no adhesive between the metal layers so they are allowed to freely move over each other at midspan and over the idler pulley. This helps to reduce the stress in the layers of the belt while the plurality of layers provides a high stiffness and strength. Instead, the multiple metal layers or plies 902A-902N are joined together at both ends, such as by a tab 912 at one or both ends as illustrated in FIG. 7D. The layers may be joined to the tab 912 by welding in one embodiment of the invention.

In a two strap system in the third link, drive strap 426B is reverse bent over the idler pulley in comparison with how it wraps around the joint pulleys. That is, one side of the drive strap wraps around the joint pulleys while the opposite side wraps around the idler pulley. Drive strap 426B may include antifriction layers (not shown) between its metal plies to reduce stress that may be introduced by the reverse bend.

To improve chassis grounding and signal routing in the third link between the second and fourth links, an electrical mechanical strap stack 950 (also referred to as an electromechanical strap stack 950) may be used in the robotic surgical arm.

Referring now to FIG. 7B, a side view of the electromechanical strap stack 950 is illustrated to provide improved chassis grounding and signal routing between the second and fourth links of the robotic surgical arm. In FIG. 7C, a cross sectional view of the electro-mechanical strap stack 950 is illustrated. The electro-mechanical strap stack 950 has substantially flat components including the drive strap 426 and the flex signal cabling 552 and/or the ground strapping 502.

Referring to FIGS. 7B-7C, the flex signal cabling 552 includes one or more flexible cables 917A-917N. Within each of the flexible cables 917A-917N are one or more flat electrical signal lines 918A-918M surrounded by an insulating material 920. In one embodiment of the invention, two flexible cable straps 917A-917B are utilized.

The ground strapping 502 includes one or more ground straps 915A-915B. In one embodiment of the invention, two ground straps 915A-915B are used. At each end, there is a fastener 790 coupling the ends of the ground strapping 502 to the pulleys 408B, 410, as illustrated in FIG. 7A.

The metal drive strap 426A of the electro-mechanical strap stack 950 includes one or more layers of metal 902N-

902B. In one embodiment of the invention, six metal layers are used to form the metal drive strap 426A.

With reference to FIG. 7C, in one embodiment of the electro-mechanical strap stack 950, its components and dimensions are (1) the metal drive strap 426A: 0.25" wide× 0.005" thick×6 plies; (2) BeCu ground strapping 552: 0.25" wide×0.004" thick×2 straps; and (3) Flex signal cabling 502: 0.24" wide×0.007" thick×2 cables.

Referring now to FIG. 7D, a side view of an end portion of the metal drive strap 426A is illustrated. Strap 426A includes metal layers 902A-902N. The metal layers or plies 902A-902N each have substantially the same width and thickness. The metal layers 902A-902N may be joined together at one or both ends of the strap by a tab 912 as illustrated in FIG. 7D. The metal layers may be joined to the tab 912 by welding in one embodiment of the invention. Alternatively, one end of the strap may have the metal layers 902A-902N joined together by a tensioning block 1312 as illustrated in FIG. 11B for example.

The multi-ply metal straps are an enabling technology for the robotic surgical arm due to their high stiffness and strength, zero backlash, low hysteresis, low friction, compact packaging, and redundant construction for safety. Their ability to bend around idler pulleys in the third link (Link 3) 343 also enables the hockey-stick shape for proper kinematics and range of motion.

In a preferred embodiment of the invention, three strap drive system is used in the third link 343 to couple between the joint pulleys to avoid use of an antifriction layer between plies of the strap 426B in the two strap drive system 700.

Referring now to FIG. 8, a perspective view of a three-strap drive system 800 used in a third link 343' is illustrated. The system 800 includes the three drive straps 426A, 827, 828; joint drive pulleys 408B', 410'; and idler pulley 412'. Alternatively, two idler pulleys could be used; one for strap 426A, and another for straps 827,828. In the preferred embodiment of the invention, each of the straps partially wraps around each pulley side-by-side over a wrap angle with first ends of straps 827,828 and two ends of strap 426A being rigidly coupled to the respective joint pulleys 408B', 410' and second ends of straps 827,828 being coupled to the idler pulley 612' so that no backlash occurs. The straps 426A, 828 are partially wrapped around the joint pulley 408B' so they will also move in opposite directions when the links are moved. The straps 426A, 827 are partially wrapped around the joint pulley 410' so they will also move in opposite directions when the links are moved. That is, the ends of straps 426A,828 are wrapped around joint pulley 408B' in opposite directions and the ends of straps 426A,827 are wrapped around joint pulley 410' in opposite directions. However, while the ends of straps 827,828 are wrapped around idler pulley 412' in opposite directions, they move in the same direction (from left to right) as the links are moved. Even though the three straps are routed side by side in the link housing, effectively they act as one continuous loop between the joint pulleys. However, the straps may be used instead of a loop as the pulleys pivot less than three hundred sixty degrees.

The idler pulley 412' is used in the system 800 to negotiate the bend in the third link (Link 3) 343' (i.e.—hockey-stick shaped link). In one embodiment of the invention, one end of the straps may be used to generate tension in each strap between the pulleys. In another embodiment of the invention, the idler pulley 412' may be used to tension the straps. The idler pulley 412' is a passive idler pulley.

To improve electrical conduction (e.g., chassis grounding and/or signal routing) in the third link between the second and fourth links, an electrical mechanical strap stack 950 (also referred to as an electro-mechanical strap stack 950) may be used in the robotic surgical arm with the three-strap drive system 800.

In FIG. 8 illustrating the three-strap drive system 800, the electro-mechanical strap stack 950 is illustrated and includes the metal strap 426A as well as the ground strapping 502 and/or the flexible signal cabling 552. The electro-mechanical strap stack 950 was previously discussed in detail and is incorporated here by reference. On each side of third link 343', there is a clamp 701 for the flexible signal cabling 552 to keep a portion thereof wrapped around a portion of the pulleys 408B',410'. At each end of the ground strapping 502 there is a fastener 790 coupling the ends to the pulleys 408B', 410'.

Strap Guide Bearing System

In a situation where straps or belts span long distances and pass over idler pulleys, they must be controlled laterally so that they do not wander off of pulleys. Due to variation in manufacturing tolerances of the straps, pulleys and other components, they sometimes wander off of a pulley that is not sufficiently wide enough to handle the variation.

To provide a compact and narrow robotic surgical arm to avoid collisions with other equipment, it is desirable to use narrow idler pulleys. With narrow idler pulleys, proper tracking of straps over idler pulleys is key to avoid strap failure. To keep straps properly tracking on narrow pulleys, a strap guide bearing system may be used. Near the idler puller 412' in the third link 343', the electro-mechanical strap stack 950 may be routed through a guide bearing system 1000 that includes side pulleys 1010A, 1010B as illustrated in FIG. 9.

Figure 9:
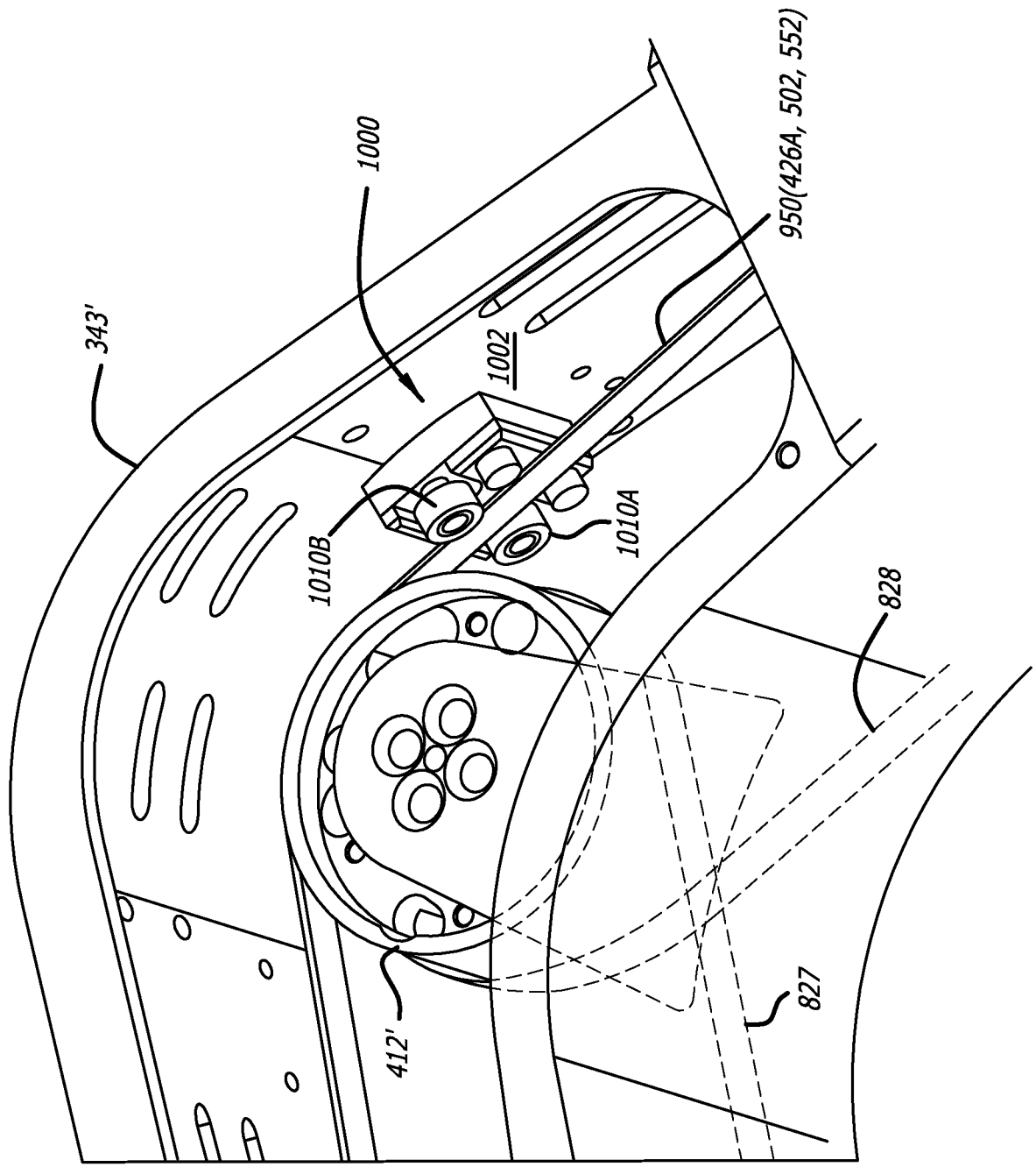
FIG. 9 illustrates a perspective view of a strap guide system in the third link of the robotic surgical arm to track the strap onto the idler pulley.

Referring now to FIG. 9, the third link 343' of the robotic surgical arm is illustrated with a three-strap drive system. The electro-mechanical strap stack 950 including the drive strap 426A extends a long distance between joint pulley 408B' and joint pulley 410'. In contrast, straps 827 and 828 are constrained laterally by their attachment to the idler pulley 412', and a strap guide system is unnecessary for these straps. To keep the electro-mechanical strap stack 950 properly tracking on the idler pulley 412', a strap guide system 1000 is provided in the third link 343'. The strap guide system 1000 is mounted inside the housing of the third link 343' to an inside surface 1002 such that its pulleys 1010A and 1010B straddle the electro-mechanical strap stack 950. In this manner, the sides of the electro-mechanical strap stack 950 are guided by the pulleys 1010A-1010B to maintain proper tracking on pulley 412'.

As mentioned previously, in the three strap system 800, only one strap guide system 1000 is needed in the third link 343' for belt 426A. In the two strap drive system 700, two strap guide systems 1000 are utilized in the third link 343 as both straps cover a long distance between pulleys. One strap guide system 1000 is provided for strap 426A and a second strap guide system 1000 is provided for strap 426B.

Figure 10A:
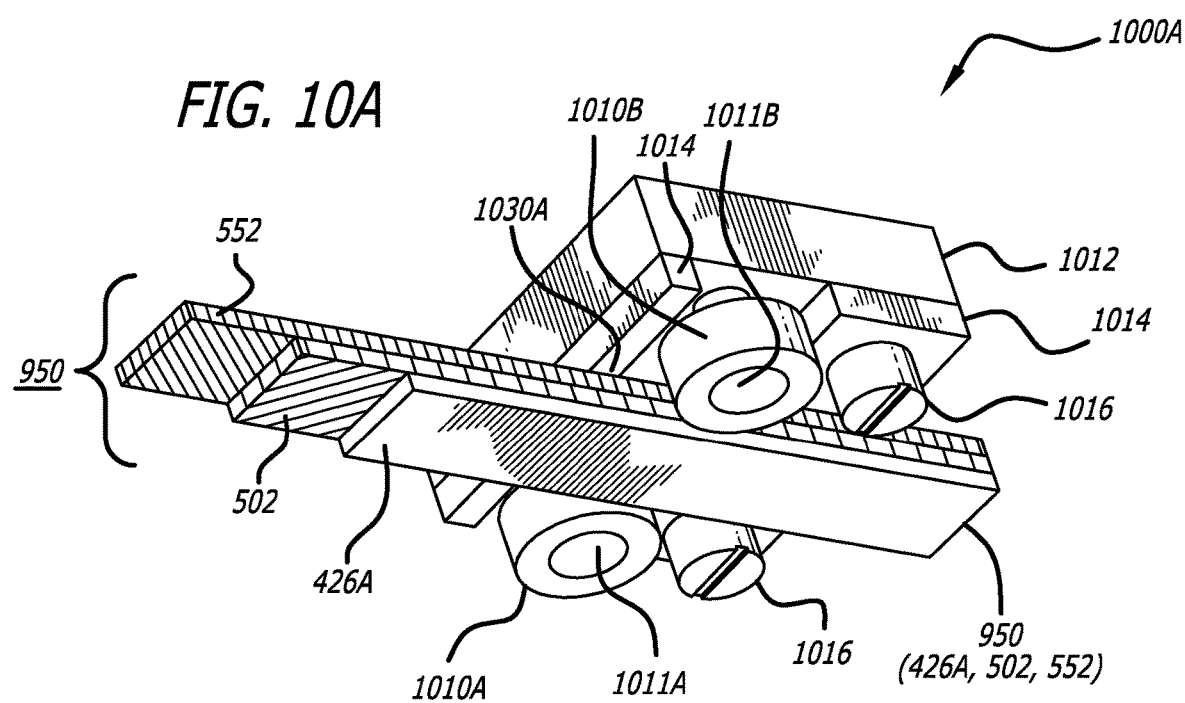
FIGS. 10A-10B illustrate alternate embodiment of the strap guide bearing system that may be used in FIG. 9.
Figure 10B:
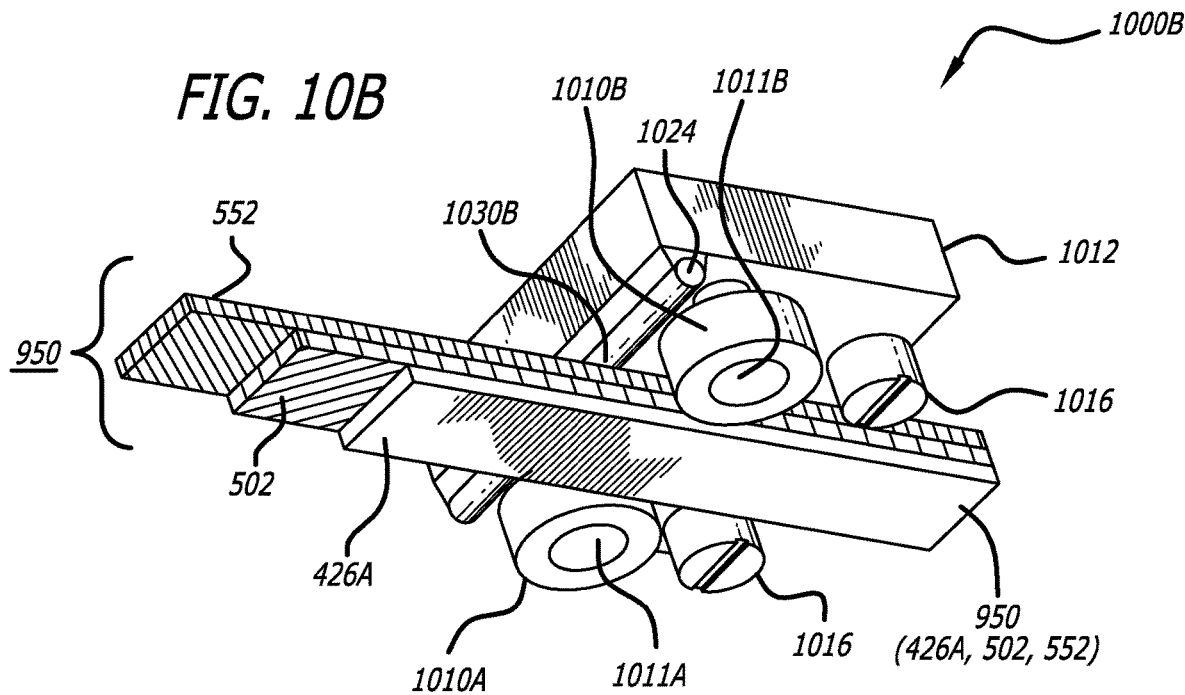

FIGS. 10A-10B illustrate alternate embodiments of the strap guide system 1000.

Referring now to FIG. 10A, the electro-mechanical strap stack 950 is better illustrated going through the guide bearing system 1000A. The guide bearing system 1000A keeps the elements of the electro-mechanical strap stack 950 stacked more tightly upon each other, and constrained laterally from wandering off pulley 412'. In case one or more layers of the electrical cable 552 and/or the ground strapping 502 lift up and away from the drive strap 426A, (i.e., puffing), the anti-friction pads 1014 can pivot them back down onto the drive strap 426A.

The anti-friction pad 1014 may be coupled up against the mounting block 1012 by the fasteners 1016. The anti-friction pad 1014 reduces abrasion on the flat flex cables 552 and ground straps 502 riding on the strap 426A by keeping them from puffing up too much over the idler pulley 612' when they are under stress. The length of the anti-friction pad 1014 is substantially parallel to the length of the belt. The anti-friction or anti-abrasion pad 1014 may be a PTFE pad, a Teflon pad, or a material having a surface with a low coefficient of friction.

Note that ordinarily the metal strap 426A, the flat flex cables 552, and ground straps 502 do not ride up against the anti-friction pad 1014. Instead there is a gap 1030A between the anti-friction pad 1014 and the electro-mechanical strap stack 950. However, one or more layers of the electro-mechanical strap stack 950 may puff up, such as the flat flex cables 552 and/or ground straps 502, and the anti-friction pad 1014 is there to push back down on them to hold the electro-mechanical strap stack 950 together around the idler pulley.

The mounting block 1012 is formed of aluminum in one embodiment of the invention. The rollers/pulleys 1010A-1010B are ball bearings in one embodiment of the invention. The dowel pins 1011A-1011B are press fit and/or glued into the center race of the bearings to secure them to the mounting block 1012.

Referring now to FIG. 10B, an alternate strap guide system 1000B is illustrated. Strap guide system 1000B is similar to strap guide system 1000A of FIG. 10A. There are a number of duplicate elements having the same reference numbers and their description is incorporated here by reference. However, instead of an anti-friction pad 1014, a roller 1024 parallel to the width of the electro-mechanical strap stack 950 is used to push down on its elements if they or any other strap puffs up near the idler pulley 412' that might be riding on top of the metal drive belt 426A. Ordinarily, the electro-mechanical strap stack 950 does not ride up against the roller 1024. Instead, there is a gap 1030B between the electro-mechanical strap stack 950 and the roller 1024.

The belt guide bearing system 1000 is compact and reliably keeps the electro-mechanical strap stack 950 tracking on the narrow idler pulley or pulleys. The electro-mechanical strap stack 950 is guided by the pulleys 1010A-1010B of the belt guide bearing system 1000. In this manner, the belt guide bearing system 1000 may be used to control the tracking of the flat flex cables, the beryllium copper ground strap, and the tensioned metal straps in a robotic surgical arm.

Figure 11A:
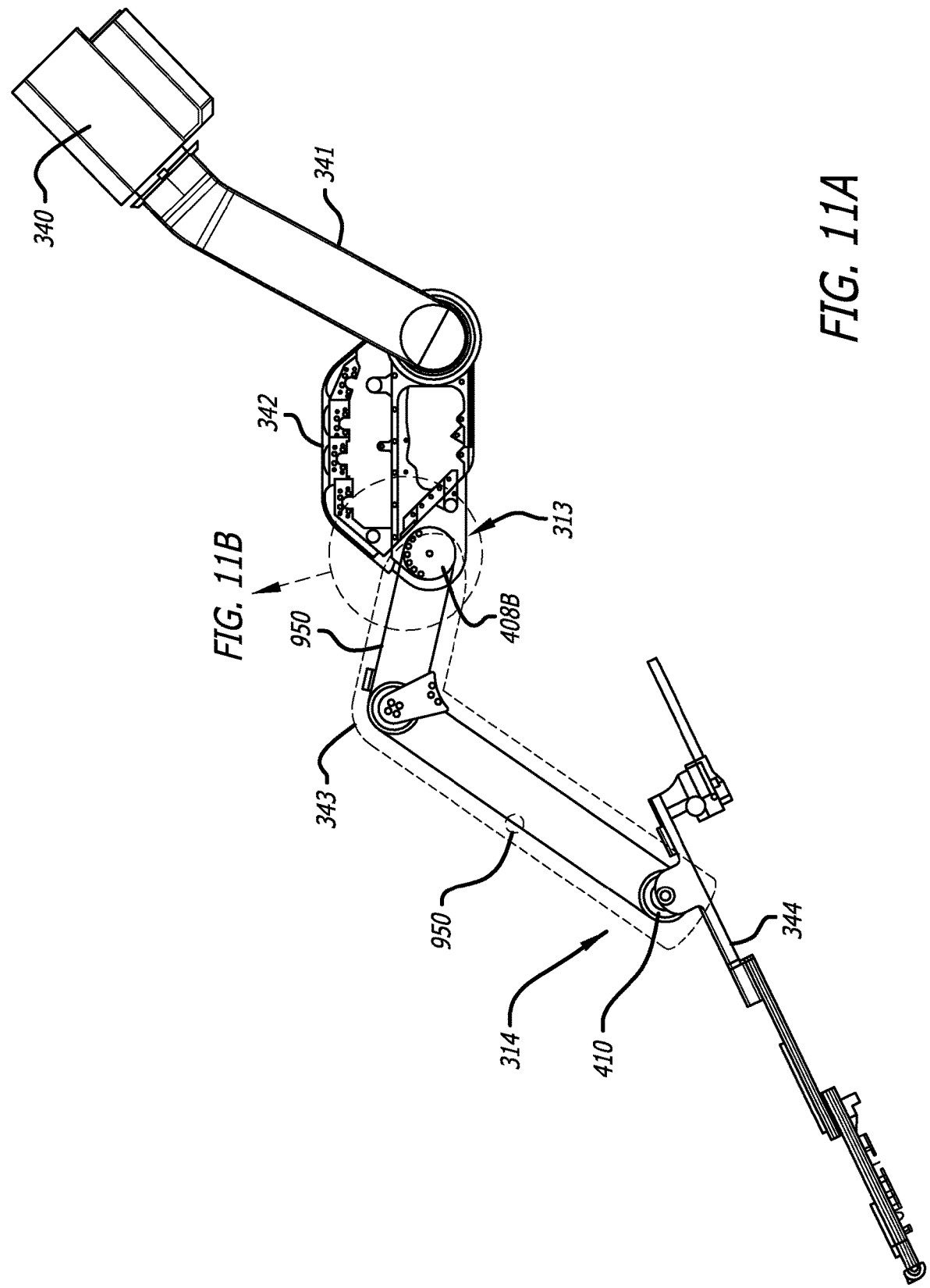

Referring now to FIG. 11A, a schematic diagram of the electro-mechanical strap stack 950 routing within the third link (link 3) 343 is illustrated. At the third joint 313 and the fourth joint 314, the electro-mechanical strap stack 950 separates into its component parts of flex signal cabling 552, ground strapping 502, and drive strap 426A.

Referring now to FIG. 11B, a magnified view of the third joint 313 is illustrated. The electro-mechanical strap stack 950 wraps over a portion of the pulley 408B, as illustrated. Pulley 408B is rigidly coupled to the second link 342.

As illustrated in FIG. 11B, the metal strap 426A wraps around a portion of pulley 408B and couples thereto through it's tensioning block 1312. With the metal strap 426A and the tensioning block 1312 both being formed of metal and coupled by a fastener 1313 (e.g., a tensioning screw) which is coupled to the pulley 408B, the metal drive strap 426A couples to the pulley 408B.

The ground strapping 502 is also wrapped around a portion of the pulley on top of a portion of the metal drive strap 426A and has an opening near its end through which a fastener 1112, such as a screw or bolt, fastens the ground strap 502 to a portion of the outer surface of the pulley 408B. The pulley 408B is conductive and is rigidly coupled to the second link 342. Thus, the ground strap 502 electrically couples to the second link 342 via the pulley 408B.

The flexible signal cabling 552 (a pair of flexible signal cables in one embodiment of the invention) also wrap around a portion of the pulley 408B on top of a portion of the ground strapping 502 and are tightly coupled thereto by a pulley cable clamp 1100 having a hockey stick shaped wall 1101 as illustrated. One end of the flexible signal cabling 552 is coupled to the control printed circuit board 531.

As previously mentioned, the pulley cable clamp 1100 has a hockey stick shaped wall 1101 to secure the flexible signal cabling 552 and the ground strapping 502 around a portion of the pulley 408B. A mounting flange 1102 of the pulley cable clamp 1100 couples it to the second link 342 by means of one or more fasteners 1104, such as screws or bolts.

Referring now to FIG. 12A, a schematic view of the electro-mechanical strap stack 950 is illustrated routing through the third link (link 3) 343 between the second link 342 and the fourth link 344. As discussed previously, the electro-mechanical strap stack 950 separates into its component parts of flex signal cabling 552, ground strapping 502, and drive strap 426A at the third joint 313 and the fourth joint 314 of the robotic surgical arm.

Referring now to FIG. 12B, a magnified view of the fourth joint 314 is illustrated with the separation of each of the constituent components of the electro-mechanical strap stack 950.

The metal strap 426A wraps around a portion of the pulley and is coupled to pulley 610 by a tab 912 within a pocket 1202. In this manner, with the tab 912 and strap 426A both being formed of metal, the metal drive strap 426A is electrically coupled to pulley 410 at one end. Pulley 410 is conductive and rigidly coupled to the fourth link 344. Thus, the strap 426A is electrically coupled to the fourth link 344 through the pulley 410.

The ground strapping 502 also wraps around a portion of the pulley 410 stacked on top of a portion of the metal strap 426A. The ground strapping 502 has an opening at an end to receive a fastener 1112, such as a screw or bolt. The fastener 1112 is inserted through the opening in the strapping 502 and screwed into pulley 410 to electrically couple the ground strap 502 thereto.

The flexible signal cabling 552 (two flexible signal cables in one embodiment of the invention) wraps around over a portion of the pulley 410 on top of the ground strapping 502. The flexible signal cabling 552 is pinched against the ground strapping 502 by a second pulley cable clamp 1200. Slack in the flexible signal cabling 552 (both flex cables) is provided at the ends of the flexible signal cabling 552. One end of the flexible signal cabling 552 is coupled to the interconnect printed circuit board 532 in fourth link 344. As shown in FIG. 5B, the other end of the flexible signal cabling 552 is coupled to the control printed circuit board 531.

The second pulley cable clamp 1200 is shaped to secure the flexible signal cabling 552 and the ground strapping 502 around a portion of the pulley 410 at the fourth joint 314. A mounting flange or bracket 1202 of the pulley cable clamp

1200 couples it to the fourth link 344 by means of one or more fasteners 1204, such as screws or bolts.

Metal drive straps for driving the pitch of the linkages of the robotic surgical arm also help to ground the chassis of the robotic surgical arm since they are electrically conductive. Using the existing metal drive straps of the drive-train to accomplish grounding, reduces and possibly eliminates the need to add additional ground wires or ground straps. However in a preferred embodiment of the invention, one or more beryllium copper metal straps are stacked on top of stainless steel multi-ply straps to provide additional grounding. Because both of the one or more beryllium copper metal straps and the steel multi-ply straps are bent around pulleys, their bending stresses are controlled and reliability is improved over that of conventional stranded electrical wiring.

In a preferred embodiment of the invention, there are three metal straps 426A,827,828 that run through the third link (Link 3) 343' (see also FIGS. 8 and 9). The longest strap 426A connects between a pulley 408B' that is rigidly connected to the second link (Link 2) 342, and another pulley 410' that is rigidly connected to the fourth link (Link 4) 344. The longest strap 426A also wraps over an idler pulley 412', with is pivotally coupled to the third link (Link 3) 343'. This idler pulley 412' is necessary so that the straps can move inside the "hockey stick" shaped third link (Link 3).

Resting directly over the strap 426A is a group of flat electrical conductors as part of the electrical cabling 552 of the electro-mechanical strap stack 950, that are necessary to power and control components at the distal end of the manipulator or robotic arm. Because the range of rotation of the pulleys is limited to less than a revolution, the straps and the flat electrical conductors can be rigidly attached at a point to each of the pulleys at the second link (Link 2) 342 and the fourth link (Link 4) 344. The advantage of this arrangement is that the flat electrical conductors of the cabling 552 have no relative motion with respect to the second link (Link 2) 342 and the fourth link (Link 4) 344, so they can be attached to the PCBs 531-532 in the respective links. The flat electrical conductors in the cabling 552 have relative motion to the third link (Link 3) 343 as do the belts. However, this motion with respect to the third link 343 is well controlled with large bend radii, as described above.

Further, because the drive pulley 408B' at the second link (Link 2) 342 and the drive pulley 410' at the fourth link (Link 4) 344 rotate together in the same direction with the drive straps, and because the drive pulleys 408B', 410' are similarly sized, the relative motion of the flat electrical conductors of the electrical cabling 552 of the electro-mechanical strap stack 950 is well controlled such that the electrical cabling 552 can be clamped at a point to each of the pulleys at the second link (Link 2) 342 and the fourth link (Link 4) 344, respectively without much slack there-between. Particularly, as one pulley rotates and "pays out" the electrical cabling 552 of the electro-mechanical strap stack 950, the other pulley similarly rotates and "takes in" the electrical cabling 552 of the electro-mechanical strap stack 950, and vice versa. Due to this arrangement, the straps and the flat electrical conductors of the electrical cabling 552 can be clamped at a point to each of the pulleys at the second link (Link 2) 342 and the fourth link (Link 4) 344, respectively, and the flat electrical conductors of the electrical cabling 552 can also be routed from there to the PCBs 531-532 in the respective links. There of course may be a little slack in the ends of the electrical cabling 552 for coupling to the PCBs and for stretching of the belts or remote center pulley adjustments.

Because of the flat shape of the conductors in the cabling 552, the cabling 552 typically tracks over the top of the metal belts better than a round wire conductor, which has less stiffness in the transverse direction. Although the embodiments of the invention disclose the flat electrical conductors of the cabling 552 riding on top of belts, they could also just ride on top of the pulleys, without straps 426A and 502 below them.

Additionally, several flat electrical conductors can be stacked on top of each other in the electro-mechanical strap stack 950. By stacking additional layers 917 in the electro-mechanical strap stack 950 for the cabling 552, the design is highly scalable to a large number of conductors to carry signal power, signal ground, and data/control signals.

The pulleys control the bend radii of the flat flexible signal cabling 552 to a predetermined limit. Bulging loop problems are eliminated in the second and fourth links by the static pulleys 408B, 410 coupled respectively thereto. Moreover, the guide belt system 1000 is used to transversely control the position of flat flexible signal cabling 552.

Some of the advantages to the embodiments of the invention are as follows. The embodiments of the invention enable high reliability due to controlled, large bend radii and thus reduced stress and fatigue. The embodiments of the invention eliminate the dynamic bulging of a typical wire loop. The embodiments of the invention enable wiring to be internal to dynamic joints. The embodiments of the invention also provide a more compact cabling than a typical round wire bundle. The embodiments of the invention experience lower stress than a round bundle around pivoting joints, thus providing a longer cycle life. The embodiments of the invention substantially eliminate abrasion, as the flat electrical conductors have little relative motion to the pulleys, and/or straps that they rest on. Additionally, the embodiments of the invention provide for flat electrical conductors to be stacked on top of each other a part of a stacked strap or electro-mechanical strap stack. With one or more additional flat electrical conductors in the stacked strap or electro-mechanical strap stack, the design is highly scalable to a large number of conductors.

The embodiments of the invention provide highly reliable conductors through a pivoting or rotary joint, replacing a typical electrical loop of wire that may be used at the joints of robotic surgical arm. The typical electrical loop of wire bulges out as the arm moves, and its bend radii are not controlled. Often, these typical electrical loops of wire break due to bending stresses and fatigue. In comparison, the embodiments of the invention provide a more reliable robotic surgical arm.

While certain exemplary embodiments of the invention have been described and shown in the accompanying drawings, it is to be understood that such embodiments of the invention are merely illustrative of and not restrictive on the broad invention, and that the embodiments of the invention not be limited to the specific constructions and arrangements shown and described, since various other modifications may occur to those ordinarily skilled in the art. For example, the embodiments of the invention have been described with reference to a robotic surgical arm. However, the embodiments of the invention are equally applicable to other types of robotic arms and not just robotic surgical arms. Rather, the embodiments of the invention should be construed according to the claims that follow below.

What is claimed is:

1. A robotic arm comprising:
   a first driver pulley rigidly coupled to a first link of a plurality of links pivotally coupled in series together at a plurality of joints to form a linkage assembly to pitch the robotic arm;
   a second driver pulley rigidly coupled to a second link of the plurality of links;
   an idler pulley rotatably coupled to a bent third link between the first and second links;
   a drive strap routed between the first driver pulley and the second driver pulley and over the idler pulley in the third link;
   an electrical cable strap routed over the drive strap in a stacked configuration with the drive strap, between the first driver pulley and the second driver pulley and over the idler pulley, the electrical cable strap configured to carry electrical signals along the robotic arm; and
   a stacked strap guide system located proximate the idler pulley, the stacked strap guide system including one or more guide pulleys to laterally constrain the electrical cable strap and the drive strap in the stacked configuration;
   wherein the idler pulley is configured to negotiate the drive strap and the electrical cable strap around the bend in the third link;
   wherein the electrical cable strap is stacked on top of the drive strap for the entirety of its length but for portions at the first and second ends of the electrical cable strap coupled respectively to the first and second electrical interfaces; and
   further wherein, the electrical cable strap is not bonded to the drive strap but is mechanically held in a stacked position on top of the drive strap by cable clamps proximate the first and second ends of the electrical cable.

2. The robotic arm of claim 1, further comprising a ground strap, in stacked configuration with the drive strap and the electrical cable strap, to improve chassis grounding.

3. A robotic arm comprising:
   a first driver pulley rigidly coupled to a first link of a plurality of links pivotally coupled in series together at a plurality of joints to form a linkage assembly to pitch the robotic arm;
   a second driver pulley rigidly coupled to a second link of the plurality of links;
   an idler pulley rotatably coupled to a bent third link between the first and second links;
   a drive strap routed between the first driver pulley and the second driver pulley and over the idler pulley in the third link;
   a flat flexible signal cabling in a stacked configuration with the drive strap, the flat flexible signal cabling is wrapped at least partially around the first driver pulley and the second driver pulley and rides on the drive strap over the idler pulley, the flat flexible signal cabling configured to carry electrical signals along the robotic arm;
   wherein the idler pulley is configured to negotiate the drive strap and the flat flexible signal cabling around the bend in the third link
   wherein the flat flexible signal cabling is stacked on top of the drive strap for the entirety of its length but for the portions at the first and second ends of the flat flexible signal cabling coupled respectively to the first and second electrical interfaces; and
   further wherein, the flat flexible signal cabling is not bonded to the drive strap but is mechanically held in a stacked position on top of the drive strap by cable clamps proximate the first and second ends of the flat flexible signal cabling.

4. The robotic arm of claim 2, wherein the ground strap includes a conductive material and is stacked onto the drive strap in parallel relation.

5. The robotic arm of claim 4, wherein the ground strap includes one or more layers of beryllium copper (BeCu).

6. The robotic arm of claim 2, further comprising:
   a ground cable including a conductive material, the ground cable having a first end coupled to the first link, the ground cable extending through the first link and having a second end coupled to a chassis ground such that the plurality of links are coupled to the chassis ground by the ground cable and the ground strap.

7. The robotic arm of claim 2:
   wherein the ground strap is coupled to the first driver pulley and the second driver pulley;
   and the robotic arm further comprises
      a ground cable including a conductive material, the ground cable having a first end coupled to the first link, the ground cable extending through the first link and having a second end coupled to a chassis ground such that the plurality of links are coupled to the chassis ground by the ground cable and the ground strap.

8. The robotic arm of claim 1, wherein the electrical cable strap includes one or more flexible cables, and each flexible cable includes one or more flexible electrical signal lines.

9. The robotic arm of claim 8, wherein the one or more flexible cables and the flexible electrical signal lines are flat.

10. The robotic arm of claim 8, further comprising:
    a first printed circuit board, including the first electrical interface, in the first link, the first electrical interface coupled to a first end of the flexible cables of the electro-mechanical strap stack, and
    a second printed circuit board, including the second electrical interface, in the second link, the second electrical interface coupled to a second end of the flexible cables of the electro-mechanical strap stack.

11. The robotic arm of claim 1, wherein the stacked strap guide system further comprises one of an anti-friction pad or a roller to longitudinally constrain the electrical cable strap moving over the idler pulley.

12. A robotic arm comprising:
    a linkage assembly including a plurality of links pivotally coupled in series together at a plurality of joints, the plurality of links including a bent link, and an idler pulley rotatably coupled to the bent link;
    a strap drive-train coupled to the linkage assembly, the strap drive train including a drive strap coupled between a drive link and an instrument holder link of the plurality of links, a first driver pulley rigidly coupled to the drive link, and a second driver pulley rigidly coupled to the instrument holder link, the drive strap wrapped around a portion of the first and second drive pulleys and over the idler pulley, wherein the strap drive-train enables movement of the linkage assembly about a pitch axis; and an electrical cable strap routed over the drive strap in a stacked configuration with the drive strap, along the robotic arm; and wherein the idler pulley is configured to direct the electrical cable strap and the drive strap around the bend in the bent link;

wherein the electrical cable strap is stacked on top of the drive strap for the entirety of its length but for portions at the first and second ends of the electrical cable strap coupled respectively to the first and second electrical interfaces; and further wherein, the electrical cable strap is not bonded to the drive strap but is mechanically held in a stacked position on top of the drive strap by cable clamps proximate the first and second ends of the electrical cable strap.

13. The robotic arm of claim 12, further comprising:
a ground strap, in stacked configuration with the drive strap and the electrical cable strap, to improve chassis grounding.

14. The robotic arm of claim 12, wherein
the electrical cable strap includes one or more of flat electrical signal lines to provide signal routing.

15. The robotic arm of claim 13, wherein
the ground strap includes a conductive material and is stacked onto the drive strap in parallel relation.

16. The robotic arm of claim 15, wherein
the ground strap includes one or more layers of beryllium copper (BeCu).

17. The robotic arm of claim 15, further comprising:
the ground strap electrically couples to a ground cable including a conductive material, the ground cable extending through other links of the plurality of links to a chassis ground such that the plurality of links are coupled to the chassis ground.

18. The robotic arm of claim 14, wherein
the electrical cable strap includes one or more flexible cables, and wherein each flexible cable includes one or more flexible electrical signal lines.

19. The robotic arm of claim 18, wherein
the flexible cables and flexible electrical signal lines are flat.

20. The robotic arm of claim 12, wherein
the electrical cable strap and the drive strap are routed between the drive link and the instrument holder link through a middle link of the plurality of links, and
wherein the drive strap is coupled between the first driver pulley and the second driver pulley and routed through the middle link.

21. The robotic arm of claim 20, further comprising:
a stacked strap guide system located proximate the idler pulley, the stacked strap guide system including a plurality of pulleys on each side of the electrical cable strap and the drive strap which are perpendicular to a direction of stacking and a direction of driving of the electrical cable strap and the drive strap, to laterally constrain the electrical cable strap and the drive strap in the stacked configuration.

22. The robotic arm of claim 21, wherein
the stacked strap guide system further comprises one of an anti-friction pad or a roller to longitudinally constrain the electrical cable strap and the drive moving over the idler pulley.

23. The robotic arm of claim 3, further comprising
a ground strap in the stacked configuration with the drive strap and the flat flexible signal cabling, the ground strap to improve chassis grounding.

24. The robotic arm of claim 3, further comprising:
a first printed circuit board, including the first electrical interface, in the first link, the first electrical interface coupled to a first end of the flat flexible signal cabling, and
a second printed circuit board, including the second electrical interface, in the second link, the second electrical interface coupled to a second end of the flat flexible signal cabling.

25. The robotic arm of claim 3, further comprising:
a stacked strap guide system located proximate the idler pulley, the stacked strap guide system including a plurality of guide pulleys on each side of the electrical cable strap and the drive strap which are perpendicular to a direction of stacking and a direction of driving of the electrical cable strap and the drive strap, to laterally constrain the electrical cable strap and the drive strap in the stacked configuration.

26. The robotic arm of claim 23, further comprising:
a ground cable including a conductive material, the ground cable having a first end coupled to the first link, the ground cable extending through the first link and having a second end coupled to a chassis ground such that the plurality of links are coupled to the chassis ground by the ground cable and the ground strap.

27. The robotic arm of claim 25, wherein
the stacked strap guide system further comprises one of an anti-friction pad or a roller to longitudinally constrain the flat flexible signal cabling and the drive strap moving over the idler pulley.

28. The robotic arm of claim 1, wherein
a first end of the electrical cable strap to couple to a first electrical interface and a second end of the electrical cable strap to couple to a second electrical interface, the electrical cable strap configured to conduct electrical signals between the first and second electrical interfaces, including providing, power to, and communicating electrical data signals with a surgical tool at the distal end of the robotic arm.

29. The robotic arm of claim 3, wherein
a first end of the flat flexible signal cabling to couple to a first electrical interface and a second end of the flat flexible signal cabling to couple to a second electrical interface, the flat flexible signal cabling configured to conduct electrical signals between the first and second electrical interfaces, including providing signal routing to a surgical tool at the distal end of the robotic arm.

30. The robotic arm of claim 12, wherein
a first end of the electrical cable strap to couple to a first electrical interface and a second end of the electrical cable strap to couple to a second electrical interface, the electrical cable strap configured to conduct electrical signals between the first and second electrical interfaces, including providing power to, and communicating electrical data signals with a surgical tool at the distal end of the robotic arm.

* * * * *